(12) United States Patent
Stevenson

(10) Patent No.: US 9,999,765 B2
(45) Date of Patent: Jun. 19, 2018

(54) SURROGATE IMPLANTED MEDICAL DEVICE FOR ENERGY DISSIPATION OF EXISTING IMPLANTED LEADS DURING MRI SCANS

(71) Applicant: Greatbatch Ltd., Clarence, NY (US)

(72) Inventor: Robert A. Stevenson, Canyon Country, CA (US)

(73) Assignee: Greatbatch Ltd., Clarence, NY (US)

( * ) Notice: Subject to any disclaimer, the term of this patent is extended or adjusted under 35 U.S.C. 154(b) by 0 days. days.

(21) Appl. No.: 15/466,939

(22) Filed: Mar. 23, 2017

(65) Prior Publication Data

US 2017/0189678 A1 Jul. 6, 2017

Related U.S. Application Data

(60) Division of application No. 14/206,152, filed on Mar. 12, 2014, which is a continuation-in-part of application No. 14/192,835, filed on Feb. 27, 2014, now Pat. No. 92,352,148.

(60) Provisional application No. 61/780,426, filed on Mar. 13, 2013.

(51) Int. Cl.
*A61N 1/37* (2006.01)
*A61N 1/08* (2006.01)
*A61N 1/375* (2006.01)

(52) U.S. Cl.
CPC ............ *A61N 1/08* (2013.01); *A61N 1/3718* (2013.01); *A61N 1/3752* (2013.01); *A61N 1/086* (2017.08)

(58) Field of Classification Search
CPC ...... A61N 1/08; A61N 1/3752; A61N 1/3718; A61N 2001/086; H01R 2201/12
See application file for complete search history.

(56) References Cited

U.S. PATENT DOCUMENTS

| | | |
|---|---|---|
| 7,225,034 B2 | 5/2007 | Ries et al. |
| 2004/0260373 A1 | 12/2004 | Ries et al. |
| 2010/0070009 A1 | 3/2010 | Barker |
| 2010/0137956 A1 | 6/2010 | Osypka |
| 2010/0174349 A1 | 7/2010 | Stevenson et al. |
| 2010/0324639 A1 | 12/2010 | Stevenson et al. |
| 2011/0022140 A1 | 1/2011 | Stevenson et al. |
| 2011/0029052 A1 | 2/2011 | McDonald et al. |
| 2013/0310900 A1 | 11/2013 | Carbunaru et al. |

OTHER PUBLICATIONS

European Search, Application 12158362.9-2305, dated Jul. 5, 2012.
Extended European Search, Application 12158362.9-1652, dated Jun. 5, 2013.

*Primary Examiner* — Tammie K Marlen
(74) *Attorney, Agent, or Firm* — Michael F. Scalise; Marc G. Martino

(57) ABSTRACT

A surrogate implantable medical device includes a thermally conductive and electrically conductive housing. A header connector block includes a header block body, where the header block body is attached to the housing. At least one connector cavity is located within the header block body and configured to be attachable to an implantable lead. At least one conductive leadwire is disposed at least partially within the header block body having a first end and a second end. The at least one conductive leadwire's first end is electrically connected to the at least one connector cavity and the at least one conductive leadwire's second end is electrically connected to the housing. The housing does not contain active electronics.

21 Claims, 33 Drawing Sheets

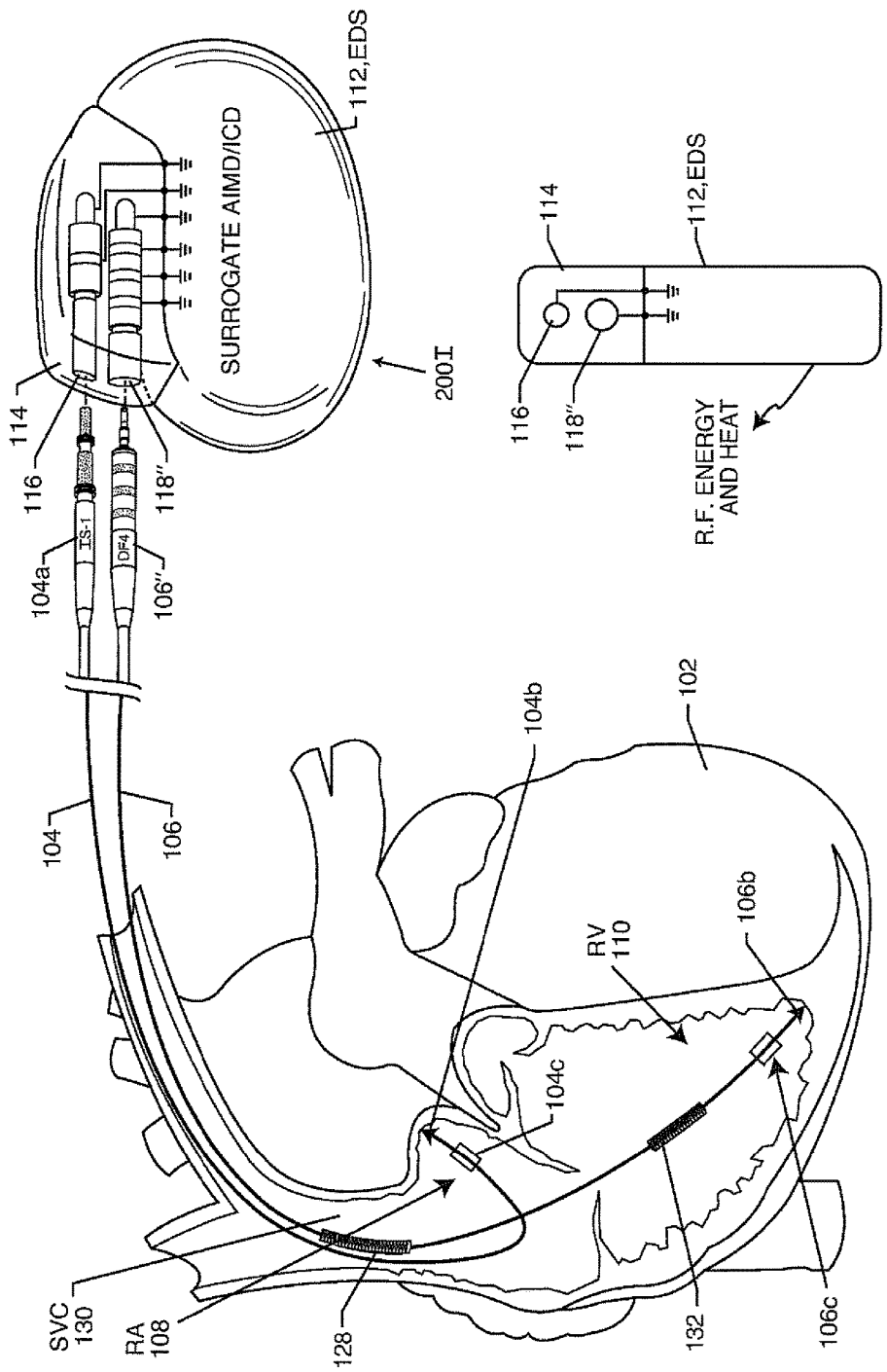

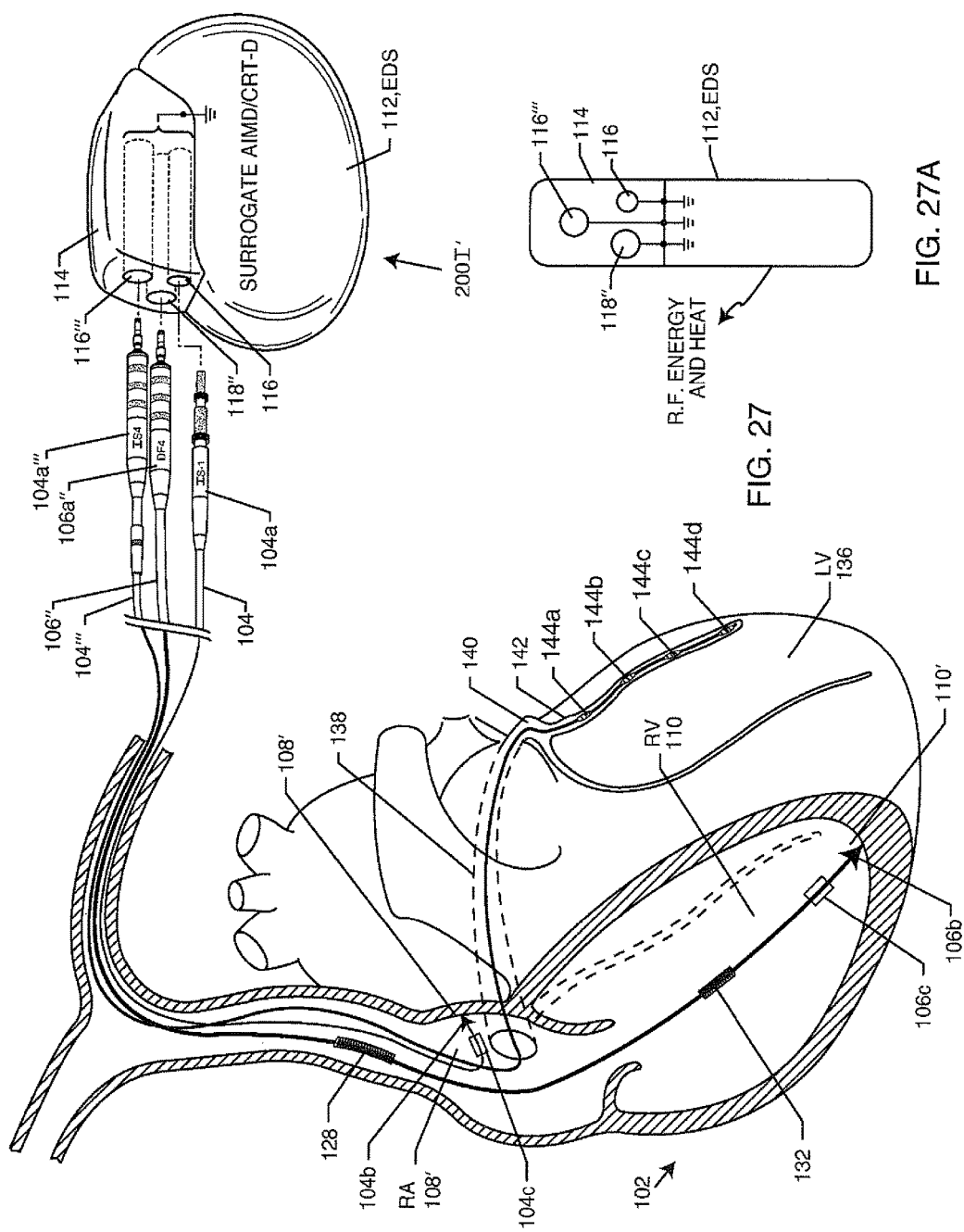

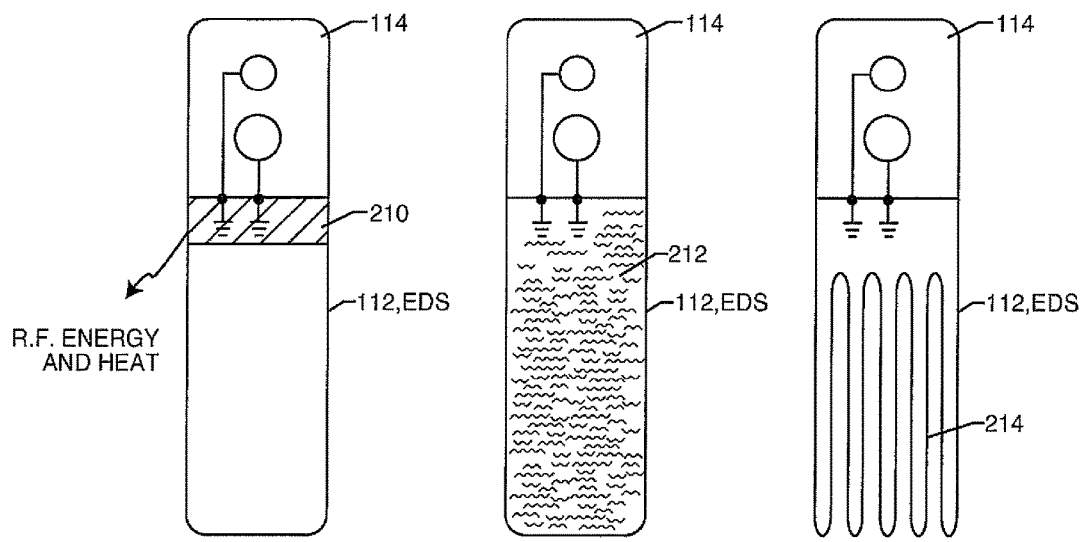
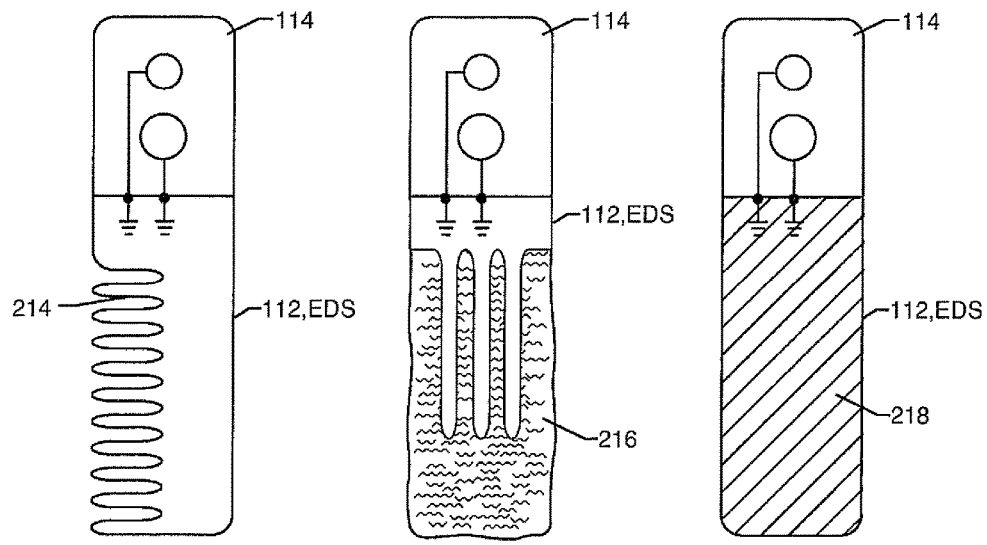

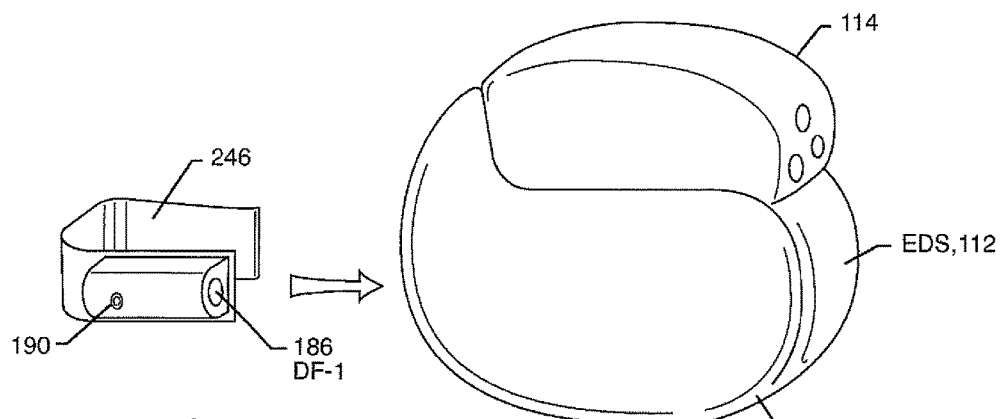
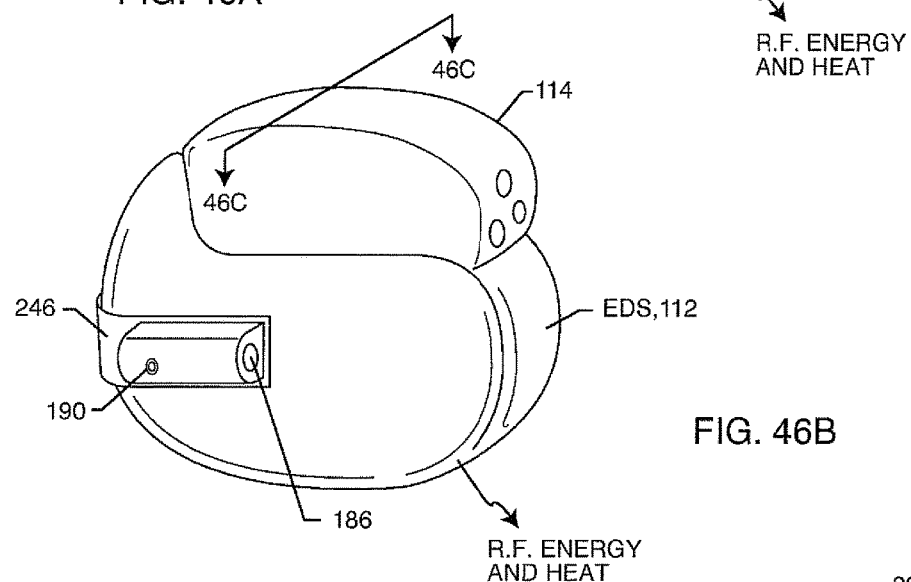
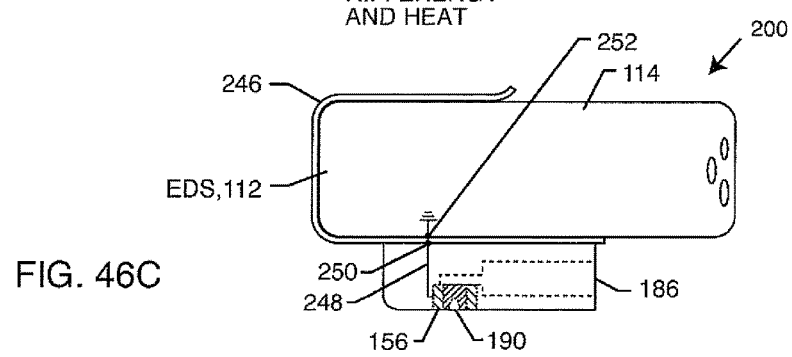

SURROGATE IMPLANTED MEDICAL DEVICE FOR ENERGY DISSIPATION OF EXISTING IMPLANTED LEADS DURING MRI SCANS

CROSS-REFERENCE TO RELATED APPLICATIONS

This application is a divisional of U.S. application Ser. No. 14/206,152, filed on Mar. 12, 2014, now abandoned, which is a continuation-in-part of application Ser. No. 14/192,835, filed on Feb. 27, 2014, now U.S. Pat. No. 9,352,148, which claims priority from U.S. provisional application Ser. No. 61/780,426, filed on Mar. 13, 2013.

DESCRIPTION

Field of the Invention

The present invention generally relates to non-MRI approved active implantable medical devices (AIMDs) such as, cardiac pacemakers, implantable cardioverter defibrillators (ICD), cardiac resynchronization therapy (CRT) devices, neurostimulators and related leads. More specifically, the present invention relates to a surrogate AIMD that is MRI compatible for temporary attachment to implanted leads during MRI scans.

Background of the Invention

Transvenous cardiac pacemakers and ICDs using leads threaded into the right sided chambers of the heart through the venous system have evolved over the years from single chamber (one implanted lead) to dual chamber (two implanted leads); then to single and eventually dual chamber ICDs. More recently with the wider recognition of the increased incidence of heart failure secondary to right sided pacing of the heart, as well to numerous other etiologies, CRT devices have been developed with left sided chamber leads delivered transvenously to endocardial locations, and/or on through the coronary sinus to left ventricular epicardial locations, and/or with a variety of transthoracic approaches to direct epicardial or intramyocardial left ventricular or left atrial stimulation sites.

In a typical prior art dual chamber defibrillator system, there is a trifurcated ventricular lead connector, with one arm providing low voltage IS-1 pace-sense function and two arms providing high voltage DF-1 connections. An advantage of this configuration was that if one of the high voltage or low voltage components of this type of lead failed, it could be corrected relatively simply by implanting a replacement single function lead, disconnecting the failed component from the pulse generator header and plugging the replacement lead's connector into that connector cavity thereby abandoning the failed lead. However, along with the AIMD, the trifurcated connector considerably increased the mass in a patient's pectoral (or other) pocket. Furthermore, the multitude of leads provided the opportunity for cross connections at the time of initial implant. Also, as the complexity of leads increased so did the chance of lead failure and increased the difficulty and risks associated with subsequent pulse generator or lead replacement/repair surgery.

The ISO 27186 Standard for DF4 and IS4 quadripolar connector systems evolved in order to replace the mechanically and functionally complex trifurcated connector with a single lead connector encompassing multiple sequential electrodes and functions requiring only a single set screw for lead fixation and electrical activation of the pin electrode. This minimized the number and size of connector cavities (ports) in defibrillator headers. In turn, this simplified surgical implant procedures and reduced the risk of technical errors. However, lead conductor failures, particularly of IS4 and DF4 style leads have still occurred.

Failure of an implanted medical lead can occur for a variety of reasons, including dislodgement at or migration from the electrode-tissue interface, complete or partial fracture or breakage of a lead conductor, abrasion or cracking or other forms of lead insulation disruption leading to low insulation resistance and low impedance measurements. Low insulation resistance can occur between a lead conductor and body fluid or between a lead conductor and adjacent lead conductors. Other reasons for failure include an increase in lead conductor impedance, an Increase of the pacing capture threshold, or Just the failure to deliver appropriate, effective or optimal therapy. As defined herein, a lead conductor failure may include one or more of any of the aforementioned conditions.

When a lead falls it is not always practical to extract an IS4 or DF4 lead even if a single conductor or function has failed. The lead extraction procedure becomes particularly more difficult as the duration of implantation lengthens. Over time, the lead typically becomes adhered to tissue due to the formation of scar tissue, tissue ingrowth and the like thus requiring a more invasive procedure to be performed. On the other hand, simply abandoning a defective IS4 or DF4 lead is problematic, because abandoning the old lead and implanting a new one can lead to venous occlusion and interference with closure of the tricuspid valve leaflets etc. Further, stacked ICD leads with large surface area and high voltage coil electrodes tend to induce significant fibrous tissue reaction, binding the leads together and to the surrounding tissues making extraction procedures even more hazardous. Yet extraction may in some cases become unavoidable because of the development of endocarditis or other complications.

Incorporation of the low and high voltage contacts of an older trifurcated connector defibrillator lead into the newer single DF4 (or its low voltage IS4 counterpart) has a number of functional limitations, but physically DF4 is a great improvement as it: (1) reduces the total volume of the implantable system; (2) reduces the number of set screws required to connect the lead to the defibrillator; (3) reduces the need for tissue dissection within the pocket during replacement; (4) reduces lead-on-lead interactions within the implant site or pocket; and (5) eliminates the potential for DF-1 connectors from being reversed in the defibrillator header. However all of these mechanical and procedural advantages are essentially lost if there is a failure of one of the multiple lead conductors, insulation (and/or their associated electrodes) either through damage or failure to deliver effective therapy.

A failure of one lead conductor in a DF4 system leaves the physician with several bad choices. The physician can put the patient, themselves and their surgical team through a potentially difficult lead explant/extraction surgery and then put in a new DF4 lead. This is not without significant risk. Or, the implanting physician could throw away the still functional defibrillator pulse generator and try to obtain a custom replacement pulse generator with all the original connector cavities including DF4, plus an additional DF-1 connector cavity for a case where a high voltage shocking coil component of the multifunctional lead system has failed, or, plus an additional IS-1 connector cavity where a component of the low voltage pace sense multifunctional lead system has failed. If this type of device was obtainable the physician could then plug the partially defective DF4 lead connector into the new DF4 header connector cavity, implant a new DF-1 lead or IS-1 lead, as indicated and in parallel with the pre-existing DF4 lead system, and insert it into the new header's additional DF-1 or IS-1 connector cavity. However, the new ICD would cost over $20,000 and would need to be specific to not only the DF4 component failure at hand, but also to the specific subtype of ICD being replaced, i.e., single chamber, dual chamber or resynchronization. Further, to date no manufacturer has agreed to produce the series of at least 6 custom ICDs necessary to repair all combinations of lead malfunction and ICD subtypes. The cost of maintaining the whole range of replacement devices in Inventory would also be high.

There are a number of problems with abandoned leads, including the problem of MRI RF field-induced overheating of such a lead or its distal electrode. Prior art abandoned lead components are problematic during MRI scans because they can pick up high-power RF induced energy which can lead to overheating of the lead and/or its distal electrode, which can heat up or even burn surrounding heart tissue. Implanted leads are generally less dangerous when they are connected to a pulse generator. The reason for this is that prior art pulse generators, including pacemakers and defibrillators generally have a feedthrough filter capacitor at the point of lead conductor ingress through the hermetic seal of the active implantable medical device. At high frequencies, such as for MRI RF pulsed frequencies, this EMI filter provides a low impedance path between the lead conductors and the AIMD housing which acts as an energy dissipating surface. Accordingly, in a high power MRI environment, much of the RF energy that is induced in the lead is diverted by the feedthrough capacitor where it is dissipated as a small temperature rise on the relatively large surface area of the pacemaker housing, which is usually a titanium housing. However, when a lead is abandoned, there is no place for this MRI RF energy to go other than at the distal tip electrode, which can still be in contact with biological cells. This can lead to significant overheating. For additional information regarding the danger of abandoned lead conductors, one is referred to a published paper entitled, PACEMAKER LEAD TIP HEATING IN ABANDONED AND PACEMAKER-ATTACHED LEADS AT 1.5 TESLA MRI, published in the Journal of Magnetic Resonance Imaging 33:426-431 (2011).

The safety and feasibility of MRI in patients with cardiac pacemakers is an Issue of gaining significance. The effects of MRI on patients' pacemaker systems have only been analyzed retrospectively in some case reports. There are a number of papers that indicate that MRI on new generation pacemakers can be conducted up to 0.5 Tesla (T). MRI is one of medicine's most valuable diagnostic tools. MRI is, of course, extensively used for imaging, but is also used for interventional medicine (surgery). In addition, MRI is used in real time to guide ablation catheters, neurostimulator tips, deep brain probes and the like. An absolute contra-indication for pacemaker patients means that pacemaker and ICD wearers are excluded from MRI. This is particularly true of scans of the thorax and abdominal areas. Because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the power of the MRI RF Pulsed field (Specific Absorption Rate-SAR level), programming the pacemaker to fixed or asynchronous pacing mode, and then careful reprogramming and evaluation of the pacemaker and patient after the procedure is complete. There have been reports of latent problems with cardiac pacemakers or other AIMDs after an MRI procedure sometimes occurring many days later. Moreover, there are a number of recent papers that indicate that the SAR level is not entirely predictive of the heating that would be found in implanted lead wires or devices. For example, for magnetic resonance imaging devices operating at the same magnetic field strength and also at the same SAR level, considerable variations have been found relative to heating of implanted lead wires. It is speculated that SAR level alone is not a good predictor of whether or not an implanted device or its associated lead wire system will overheat.

There are three types of electromagnetic fields used in an MRI unit. The first type is the main static magnetic field designated $B_0$ which is used to align protons in body tissue. The field strength varies from 0.5 to 3.0 Tesla in most of the currently available MRI units in clinical use. Some of the newer MRI system fields can go as high as 4 to 5 Tesla. At the recent International Society for Magnetic Resonance in Medicine (ISMRM), which was held on 5 and 6 Nov. 2005, it was reported that certain research systems are going up as high as 11.7 Tesla. This is over 100,000 times the magnetic field strength of the earth. A static magnetic field can induce powerful mechanical forces and torque on any magnetic materials implanted within the patient. This would include certain components within the cardiac pacemaker itself and or lead wire systems. It is not likely (other than sudden system shut down) that the static MRI magnetic field can induce currents into the pacemaker lead wire system and hence into the pacemaker itself. It is a basic principle of physics that a magnetic field must either be time-varying as it cuts across the conductor, or the conductor itself must move within the magnetic field for currents to be induced.

The second type of field produced by magnetic resonance imaging is the pulsed RF field which is generated by the body coil or head coil. This is used to change the energy state of the protons and illicit MRI signals from tissue. The RF field is homogeneous in the central region and has two main components: (1) the magnetic field is circularly polarized in the actual plane; and (2) the electric field is related to the magnetic field by Maxwell's equations. In general, the RF field is switched on and off during measurements and usually has a frequency of 21 MHz to 64 MHz to 128 MHz depending upon the static magnetic field strength. The frequency of the RF pulse varies with the field strength of the main static field where: RF PULSED FREQUENCY in MHz=(42.56) (STATIC FIELD STRENGTH IN TESLA).

The third type of electromagnetic field is the time-varying magnetic gradient fields designated $B_1$ which are used for spatial localization. These change their strength along different orientations and operating frequencies on the order of 1 kHz. The vectors of the magnetic field gradients in the X, Y and Z directions are produced by three sets of orthogonally positioned coils and are switched on only during the measurements. In some cases, the gradient field has been shown to elevate natural heart rhythms (heart beat). This is not completely understood, but it is a repeatable phenomenon. The gradient field is not considered by many researchers to create any other adverse effects.

It is instructive to note how voltages and EMI are induced into an implanted lead wire system. At very low frequency (VLF), voltages are induced at the input to the cardiac pacemaker as currents circulate throughout the patient's body and create voltage drops. Because of the vector displacement between the pacemaker housing and, for example, the TIP electrode, voltage drop across the resistance of body tissues may be sensed due to Ohms Law and the circulating current of the RF signal. At higher frequencies, the implanted lead wire systems actually act as antennas where currents are induced along their length. These antennas are not very efficient due to the damping effects of body tissue; however, this can often be offset by extremely high power fields (such as MRI pulsed fields) and/or body resonances. At very high frequencies (such as cellular telephone frequencies), EMI signals are induced only into the first area of the lead wire system (for example, at the header block of a cardiac pacemaker). This has to do with the wavelength of the signals involved and where they couple efficiently into the system.

Magnetic field coupling into an implanted lead wire system is based on loop areas. For example, in a cardiac pacemaker, there is a loop formed by the lead wire as it comes from the cardiac pacemaker housing to its distal TIP, for example, located in the right ventricle. The return path is through body fluid and tissue generally straight from the TIP electrode in the right ventricle back up to the pacemaker case or housing. This forms an enclosed area which can be measured from patient X-rays in square centimeters. The average loop area is 200 to 225 square centimeters. This is an average and is subject to great statistical variation. For example, in a large adult patient with an abdominal implant, the implanted loop area is much larger (greater than 450 square centimeters).

Patients that have non-MRI approved AIMDs do not currently have good options in getting an MRI scan performed. A new MRI approved pacemaker can be implanted within the patient, yet the abandoned leads become problematic. An abandoned lead can heat during an MRI procedure just as an active lead would. However, the abandoned lead is not electrically coupled to an AIMD housing and is therefore not able to dissipate its energy safely into an AIMD housing away from vital body tissue. In some of the prior art, a lead cap has been used to attach to the proximal end of the abandoned lead. The abandoned lead cap can also comprise a significant amount of mass similar to the housing of an AIMD. The abandoned lead cap is then used to help divert energy from the lead itself during an MRI procedure. However, the efficiency and size of the abandoned lead cap is subject to available space limitations inside the human body. Furthermore, a plurality of abandoned lead caps may be required when more than one lead is being abandoned. This can result in too many lead caps being implanted into a patient. A patient could have the abandoned leads removed. However, as discussed earlier this is problematic due to tissue ingrowth and other complications.

Accordingly, there is a need for a solution for patients with non-MRI approved AIMDs that will allow them to safely and easily have an MRI scan. The present invention fulfills these needs and provides other related advantages.

SUMMARY OF THE INVENTION

An exemplary embodiment of a surrogate implantable medical device includes a thermally conductive and electrically conductive housing. A header connector block includes a header block body, where the header block body is attached to the housing. At least one connector cavity is located within the header block body and configured to be attachable to an implantable lead. At least one conductive leadwire is disposed at least partially within the header block body having a first end and a second end. The at least one conductive leadwire's first end is electrically connected to the at least one connector cavity and the at least one conductive leadwire's second end is electrically connected to the housing. The housing does not contain active electronics.

In other exemplary embodiments the at least one connector cavity may comprise a plurality of connector cavities. The at least one connector cavity may comprise an ISO IS-1, IS4, DF-1 or DF4 connector cavity.

A diverter element may be connected physically and electrically in series along the at least one conductive leadwire, wherein the diverter element comprises a short circuit, a resistor, a capacitor or an L-C trap filter.

The housing may comprise a hermetic terminal, wherein the at least one conductive leadwire passes through the hermetic terminal in non-conductive relation to the housing, and wherein the diverter element is disposed on an inside of the housing.

A lead adapter may be associated with the header connector block, the lead adapter comprising a header plug electrically connected to at least two auxiliary connector cavities, where the header plug is configured to physically insert into and electrically couple to the at least one connector cavity of the header block body and where the at least two auxiliary connector cavities are configured to be respectively attachable to at least two implantable leads, wherein when the lead adapter is connected to the header connector block the at least two auxiliary connector cavities are electrically coupled to the housing.

Each of the at least two auxiliary connector cavities of the lead adapter may comprise an ISO IS-1, IS4, DF-1 or DF4 connector cavity. The lead adapter may have a low profile conforming shape, including an intermediate conformal section between the header plug and the housing for placing the at least two auxiliary connector cavities adjacent to an exterior surface of the housing when the header plug is placed within the at least one connector cavity. The lead adapter may have an exterior surface which tightly conforms to an exterior surface of the housing.

The housing may comprise a plurality of fins. The plurality of fins may be attached to a silicone substrate, where the silicone substrate comprises a thermally and/or electrically conductive additive. The housing may comprise a solid block of metal.

The housing may comprise an exterior surface, wherein the exterior surface is selected from the group consisting of a convoluted surface, a roughened surface, a plasma etching surface, a sputtering surface, a chemical etching surface, a porous coating deposition surface, a physical vapor deposition surface, a chemical vapor deposition surface, an electron beam deposition surface, a fractal coating surface, a metal nitride coating surface, a titanium nitride coating surface, a metal oxide coating surface, a metal carbide coating surface, an iridium-oxide coating surface, a nucleate high surface area morphological structure coating surface, a columnar high surface area morphological structure surface and combinations thereof.

The housing may enclose a high thermal and/or electrical conductivity substance, where the substance is selected from the group consisting of a gel, a liquid, a paste, a phase-change material and a combination thereof.

Another exemplary embodiment of the present invention discloses an auxiliary implantable medical device including a thermally conductive and electrically conductive housing receiver. A connector block comprises a block body, where the block body is attached to the housing receiver. At least one connector cavity is located within the block body and configured to be attachable to an implantable lead. At least one conductive leadwire is disposed within the block body having a first end and a second end, wherein the at least one conductive leadwire's first end is electrically connected to the at least one connector cavity and the at least one conductive leadwire's second end is electrically connected to the housing receiver. The housing receiver is configured to receive a housing of an active implantable medical device.

In other exemplary embodiments the housing receiver may comprise a clip, where the clip may be configured to slide onto and grip the housing of the active implantable medical device. The at least one connector cavity may comprise an ISO IS-1, IS4, DF-1 or DF4 connector cavity. The at least one connector cavity may comprise a plurality of connector cavities, where each of the at least one connector cavities comprises an ISO IS-1, IS4, DF-1 or DF4 connector cavity.

A lead adapter may be associated with the connector block, where the lead adapter comprises a connector plug electrically connected to at least two auxiliary connector cavities, where the connector plug is configured to physically insert into and electrically couple to the at least one connector cavity of the block body and where the at least two auxiliary connector cavities are configured to be respectively attachable to at least two implantable leads, wherein when the lead adapter is connected to the connector block the at least two auxiliary connector cavities are electrically coupled to the housing receiver.

Each of the at least two auxiliary connector cavities of the lead adapter may comprise an ISO IS-1, IS4, DF-1 or DF4 connector cavity, and wherein the connector plug comprises an ISO IS-1, IS4, DF-1 or DF4 connector plug.

Another exemplary embodiment of the present invention is a method of performing an MRI scan on a patient with an active implanted medical device (AIMD). The method includes providing a patient with an AIMD for surgery, then providing a surrogate implantable medical device (SIMD), then removing the AIMD from the patient's pre-existing AIMD pocket, then unplugging at least one proximal plug of a pre-existing implanted lead from the AIMD, then plugging the at least one proximal plug of the pre-existing implanted lead into the at least one connector cavity of the SIMD, then implanting the SIMD into the patient's pre-existing AIMD pocket, then performing and completing an MRI scan of the patient, then removing the SIMD from the patient's pre-existing AIMD pocket, then unplugging the at least one proximal plug of the pre-existing implanted lead from the SIMD, then plugging the at least one proximal plug of the pre-existing implanted lead into the AIMD or a new AIMD, and then implanting the AIMD or the new AIMD into the pre-existing AIMD pocket.

The method may also include the step of filing the patient's pre-existing AIMD pocket with sterile saline before the step of performing and completing the MRI scan of the patient.

Another exemplary embodiment of the present invention is a method of performing an MRI scan on a patient with an active implanted medical device (AIMD). The method includes providing a patient with an AIMD for surgery, then providing an auxiliary implantable medical device (IMD), then implanting the auxiliary IMD into the patient's pre-existing AIMD pocket while also attaching the auxiliary IMD's housing receiver onto a housing of the AIMD, then unplugging at least one proximal plug of a pre-existing implanted lead from the AIMD, then plugging the at least one proximal plug of the pre-existing implanted lead into the at least one connector cavity of the auxiliary IMD, then performing and completing an MRI scan of the patient, then unplugging the at least one proximal plug of the pre-existing implanted lead from the auxiliary IMD, then removing the auxiliary IMD from the patient's pre-existing AIMD pocket, and the plugging the at least one proximal plug of the pre-existing implanted lead into the AIMD.

The method may also include step of filing the patient's pre-existing AIMD pocket with sterile saline before the step of performing and completing the MRI scan of the patient.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 26 illustrates a surrogate ICD which is based on previous FIG. 4;

FIG. 26A illustrates an end view of the ICD previously described in FIG. 26;

FIG. 27 illustrates a surrogate ICD which is based on previous FIG. 5;

FIG. 27A is an end view of the device taken directly from FIG. 27;

FIG. 38A illustrates an embodiment of a surrogate AIMD with an energy dissipating area near the leadwire connection;

FIG. 38B illustrates another embodiment of a surrogate AIMD now with an energy dissipating gel filled in the housing;

FIG. 38C illustrates another embodiment of a surrogate AIMD now with energy dissipating fins in a vertical direction;

FIG. 38D illustrates another embodiment of a surrogate AIMD now with energy dissipating fins in a horizontal direction;

FIG. 38E illustrates another embodiment of a surrogate AIMD now with energy dissipating fins in a vertical direction within an energy dissipating gel;

FIG. 38F illustrates another embodiment of a surrogate AIMD now with energy dissipating mass;

FIG. 46A illustrates a novel clip of the present invention;

FIG. 46B illustrates the novel clip which has been clipped onto the AIMD housing;

FIG. 46C is a top sectional view 46C-46C taken generally from FIG. 46B;

DETAILED DESCRIPTION OF THE PREFERRED EMBODIMENTS

Reference is made to section 3 of ISO Standard 27186 as providing definitions to terms and terminology which are used to describe the present invention. Accordingly, as used herein: "bipolar" means having two poles or electrodes; "connector system" refers to an assembly consisting of a lead connector and a connector cavity that are electrically and mechanically joined; "connector cavity" is defined as a cavity within the pulse generator which is intended to receive a lead connector and an identical cavity within a secondary header; "fixation zone" is a zone located in the lead connector pin and within the connector cavity where the lead connector is mechanically secured within the connector cavity; "high-voltage" is defined as electrical potentials greater than 20 volts up to 2000 volts (Note: High-voltages are generally used for defibrillating the heart); "lead connector" or "plug" is the part of the lead that is intended for insertion into the connector cavity of a pulse generator; "lead connector contacts" are defined as conductive elements on the lead connector which include the lead connector pin and lead connector rings; "lead connector pin" is defined as the most proximal conductive element of a lead connector provided for making electrical contact as well as for securing the lead connector within the connector cavity; "lead connector ring" defines angular conductive elements on the lead connector intended for making electrical contact within the connector cavity (Note: the 4-pole or quadpolar connector (DF4 or IS4) has up to 3 lead connector rings and a lead connector pin); "lead electrode" is the distal part of a lead through which electrical impulses are transmitted to or from cardiac tissue (Note: high-voltage electrodes are capable of delivering high-voltage electrical impulses; Low-voltage electrodes are used for transmitting and sensing low-voltage impulses and are generally not suitable for delivering high-voltage); "low-voltage" defines electrical potentials less than or equal to 20 volts; "pulse generator" is any type of active implantable medical device (AIMD) and particularly those devices that deliver electrical energy to effect cardiac rhythms; "securing mechanism" is defined as a mechanism within the connector cavity intended for mechanically securing the lead connector (Note: a securing mechanism can be an active mechanism, such as a set screw or it can be a passive mechanism, such as a spring contact or self-engaging latch; It can also serve a second function of providing electrical contact with the lead connector, as is the case with a set screw); "tripolar" means having three poles or electrodes.

Figure 1:
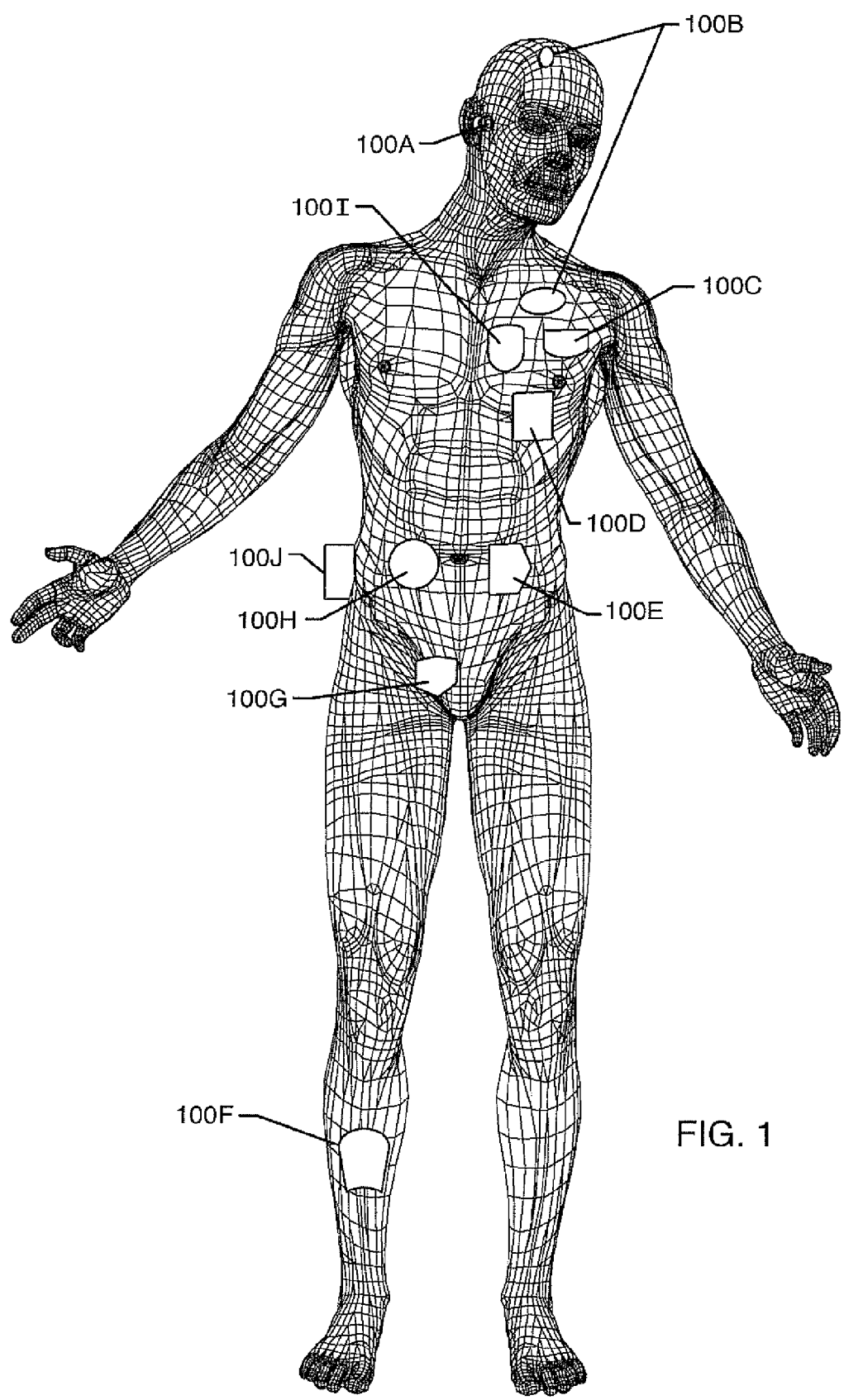
FIG. 1 illustrates a wire form drawing of a human body showing various active implantable medical devices (AIMDs)

FIG. 1 is a wire formed diagram of a generic human body showing a number of exemplary implanted medical devices. 100A is a family of implantable hearing devices which can include the group of cochlear implants, piezoelectric sound bridge transducers and the like. 100B includes an entire variety of neurostimulators and brain stimulators. 100C shows a cardiac pacemaker. 100D includes the family of left ventricular assist devices (LVAD's) and artificial hearts. 100E includes an entire family of drug pumps which can be used for dispensing of insulin, chemotherapy drugs, pain medications and the like. 100F includes a variety of implantable bone growth stimulators for rapid healing of fractures. 100G includes urinary incontinence devices. 100H includes the family of pain relief spinal cord stimulators and anti-tremor stimulators. 100I includes a family of implantable cardioverter defibrillator (ICD) devices, congestive heart failure devices (CHF), and cardio resynchronization therapy devices, otherwise known as CRT devices. 100J illustrates a family of externally worn neurostimulators which are connected to one or more implanted leads (not shown).

Figure 1A:
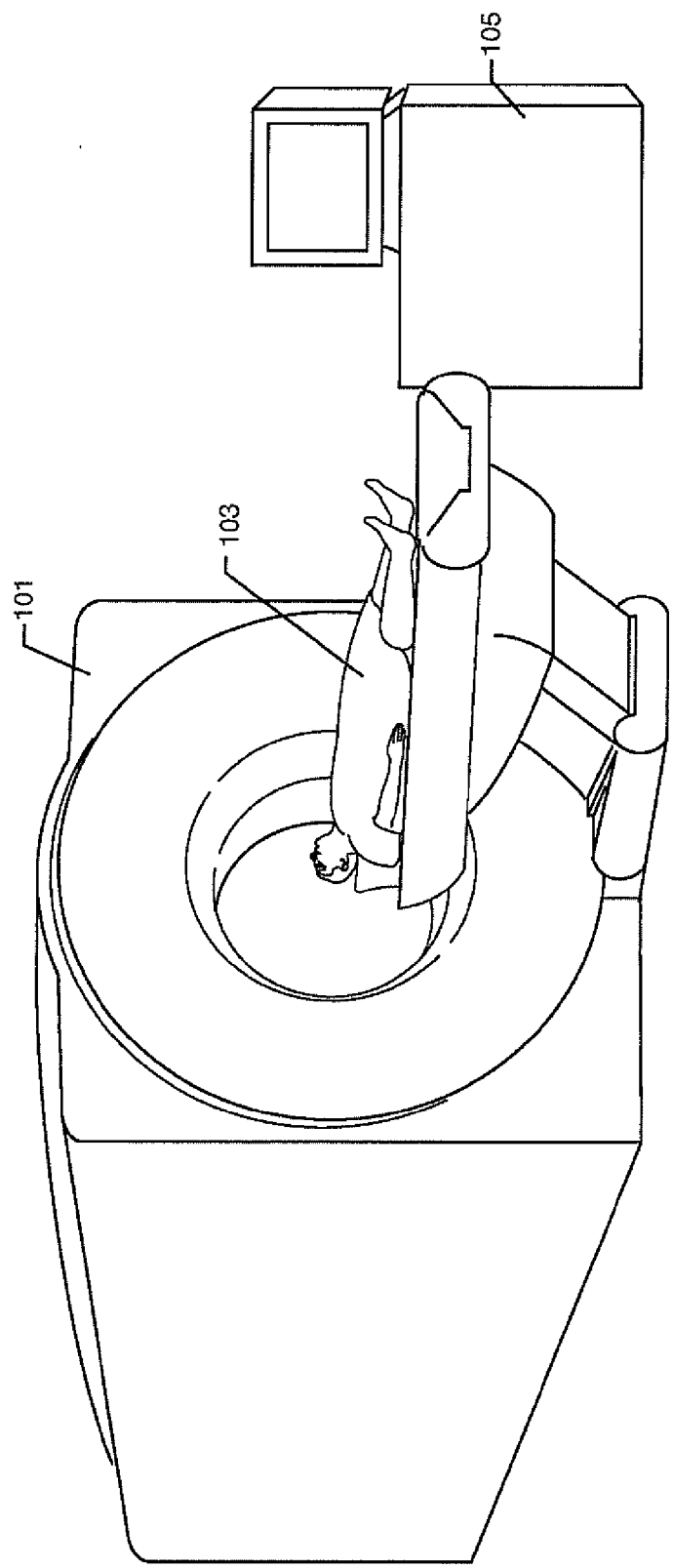
FIG. 1A illustrates a perspective view of a patient who is about to be placed into an MRI scanner.

FIG. 1A illustrates a prior art MRI scanner 101 with a patient 103 about to be positioned within the scanner. Also shown is MRI imaging processing equipment 105.

Figure 1B:
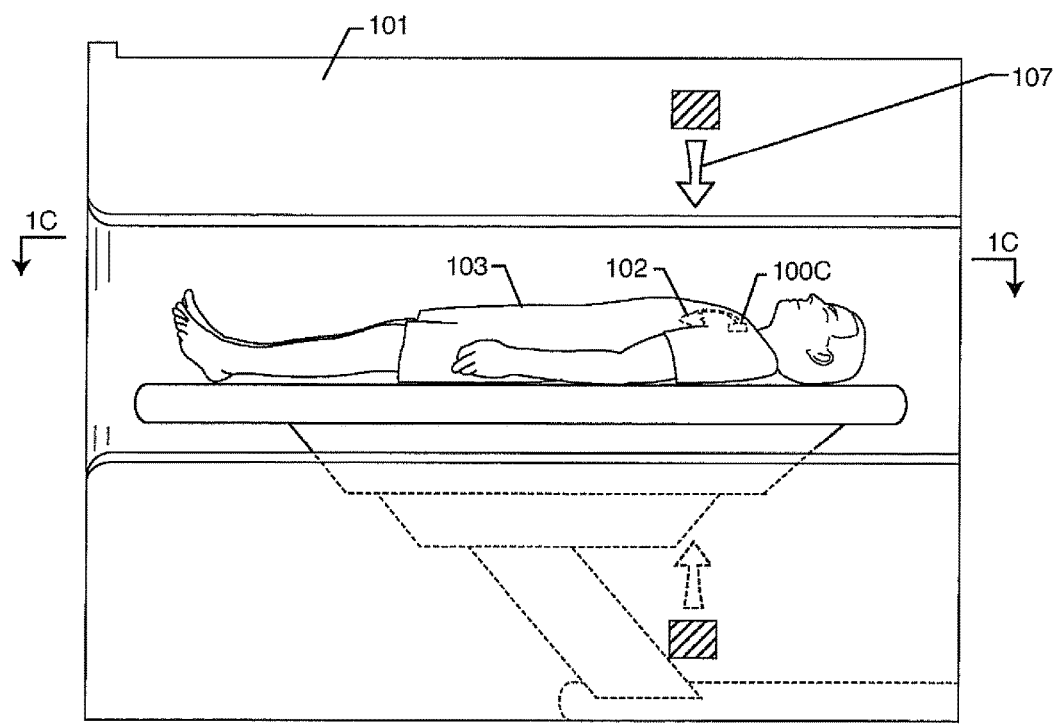
FIG. 1B illustrates a side view of the patient within the scanner showing an intense RF field impinging on the probe or catheter.

FIG. 1B illustrates a side view of the patient 103 placed inside of the scanner 101 and portrays that there is an intense RF field 107 to which the patient's entire body may be exposed. As previously mentioned this intense MRI RF-pulsed field 107 can couple to implanted leadwires of AIMDs such as a cardiac pacemaker 100C and create substantial electromagnetic forces and currents. It is very important that the distal electrodes of implanted leads 104, 106 be protected from overheating in such an environment.

Figure 1C:
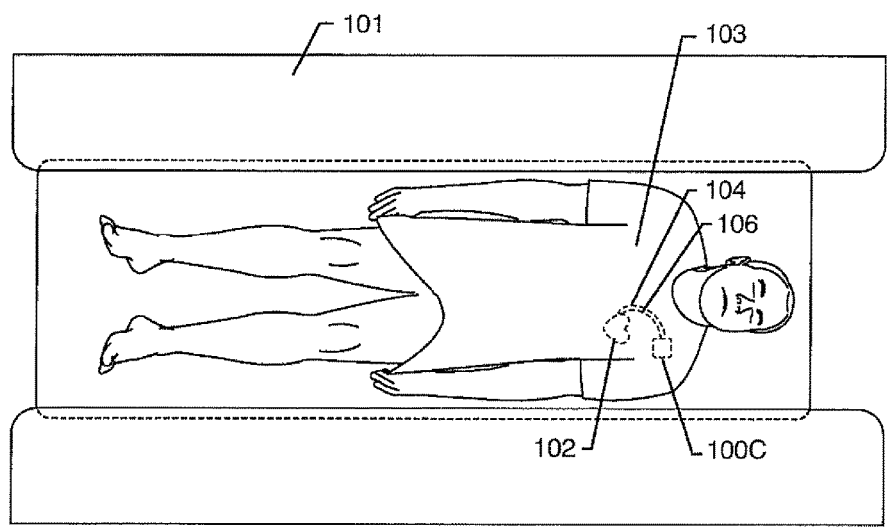
FIG. 1C illustrates a top view of the patient in the MRI scanner.

FIG. 1C is a top view of the patient 103 inside the bore of the MRI scanner 101 with an implanted pacemaker 100C with its associated cardiac leads 104,106 directed to the heart 102.

Figures 2, 2A:
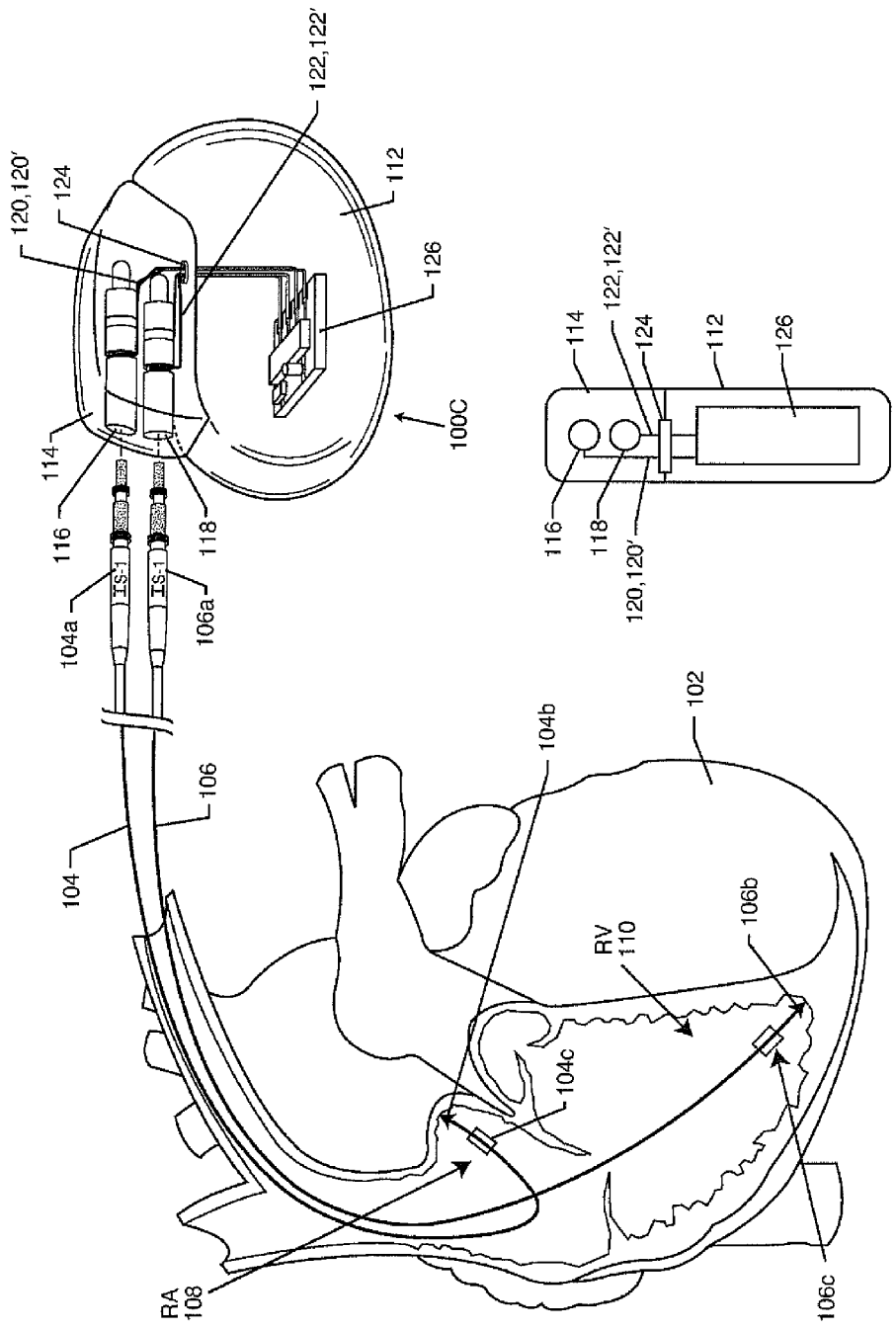
FIG. 2 illustrates a prior art dual chamber bipolar pacemaker with leads implanted into a human heart.
FIG. 2A illustrates an electrical schematic simplification of the structure of FIG. 2.

FIG. 2 shows a prior art outline diagram of the human heart 102 and a cardiac pacemaker 100C. Shown are two implanted bipolar leads 104 and 106 which both have IS-1 connectors 104a, 106a at their proximal ends. Lead 104 is routed transvenously into the right atrium (RA) 108 of the heart 102. Lead 104 is a bipolar lead, meaning that it has two conductors. One of the lead conductors terminates in the distal tip electrode 104b and the other conductor terminates in the distal ring electrode 104c. Implanted lead 106 is routed into the right ventricular cavity (RV) 110. It is also bipolar, meaning that it has two conductors, one of which is connected to the distal tip electrode 106b and the other conductor is connected to the distal ring electrode 106c. This system is known in the art as a dual chamber bipolar pacemaker 100C. The pacemaker 100C has a metallic housing 112 generally of titanium, stainless steel or the like. It also has a non-conductive header block 114 which holds connector assembly components in accordance with ISO Standard IS-1. In this case, the header 114 has two connector cavities 116 and 118 into which the IS-1 lead proximal connectors 104a, 106a can be inserted. Generally, there would be set screws to fix the connector ring and pin electrodes firmly in place (not shown). There are leadwires 120, 120', 122, 122' routed from the connector cavities 116, 118. These four leadwires 120, 120', 122, 122' are routed to a hermetic seal 124 where the wires pass through the housing 112 in non-conductive relation. It is very important that the housing 112 of the AIMD be completely hermetic to protect sensitive electronic components from body fluids, for example, those that are shown on circuit board 126.

FIG. 2A is an electrical schematic simplification of the header 114 and housing 112 shown in FIG. 2. The connector cavities 116 and 118 are shown electrically connected to the leadwires 120, 120', 122, 122' through the hermetic seal 124 to the inside of the housing 112 and electrically coupled to the circuit board 126.

Figures 3, 3A:
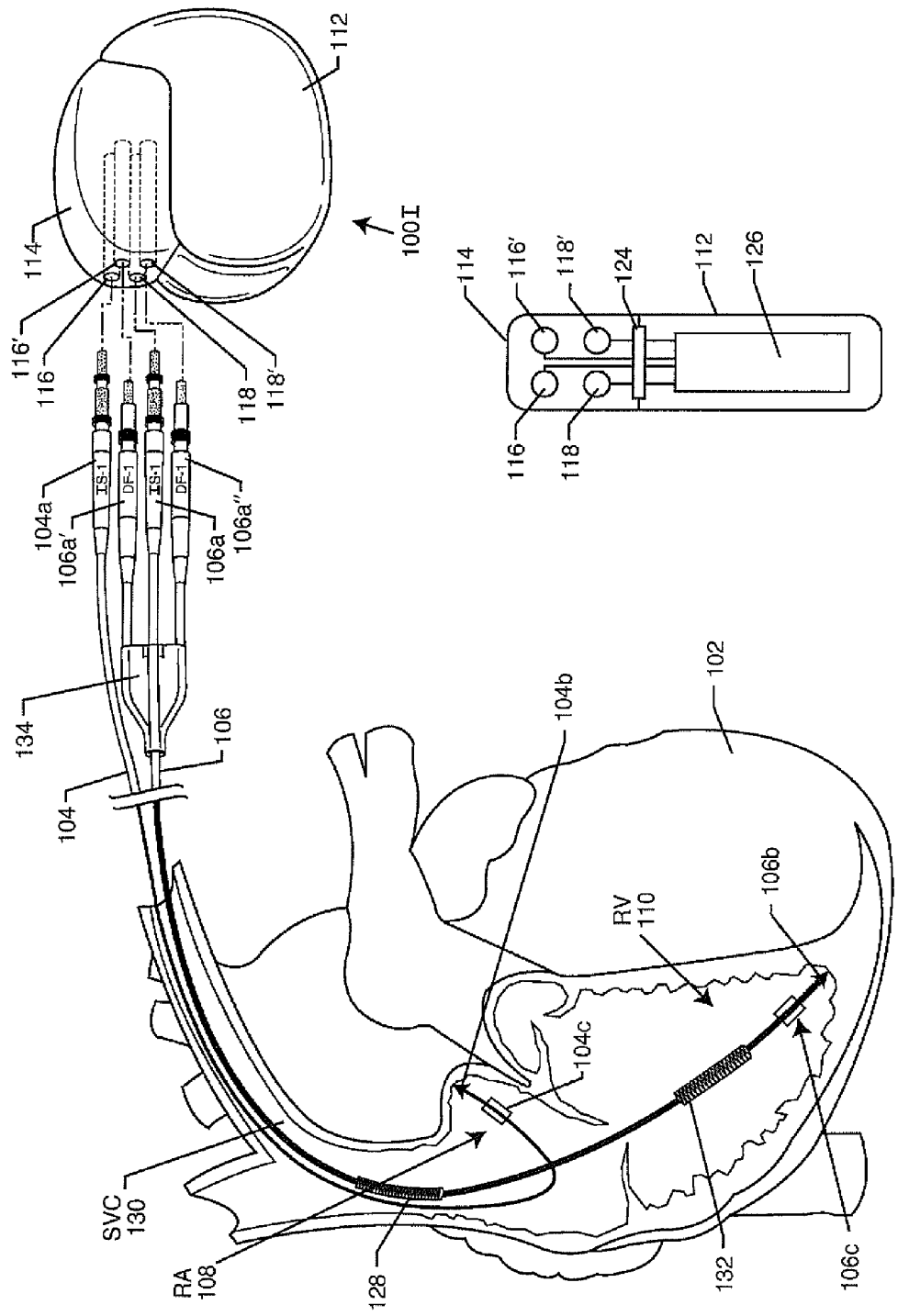
FIG. 3 illustrates a prior art dual chamber implantable cardioverter defibrillator with leads and shocking coils implanted into a human heart.
FIG. 3A illustrates an electrical schematic simplification of the structure of FIG. 3.

FIG. 3 also shows a prior art outline drawing of a human heart 102 and in this case, the device 100I is a dual chamber implantable cardioverter defibrillator. One can see that there are four connector cavities 116, 116', 118, 118' into which the IS-1, DF-1, IS-1 and DF-1 proximal connectors 104a, 106a', 106a, 106a" may be inserted. Again, there are two implanted leads 104 and 106. Bipolar lead 104 is transvenously inserted into the right atrium 108 of the heart 102. It has a distal tip electrode 104b and a distal ring electrode 104c. Quadpolar lead 106 has four conductors. Two of these conductors route to the distal tip electrode 106b and the distal ring electrode 106c. The DF-1 connectors 106a', 106a" are high-voltage conductors. One of the high-voltage connectors 104a' is routed via lead 106 to shocking coil 128, which is generally located in the superior vena cava (SVC) 130 of the heart 102. The second high-voltage shocking coil 132 is located in the right ventricle 110.

In FIG. 3, one can see that there is a trifurcated lead adaptor 134 which combines the connectors 106a', 106a, 106a" for the two high-voltage shocking coils 128, 132 along with one low-voltage tip 106b and ring 106c circuit. In the prior art, excess lead is typically wound up in the pectoral pocket, either adjacent to or around the ICD 100I. The trifurcated adaptor 134 and lead system 104, 106, as shown in FIG. 3, makes for a very bulky pectoral pocket lead arrangement as compared to the arrangement shown in FIG. 2. In addition the four separate connectors and associated proximal lead segments tend to create crisscrossing tissue ingrowth paths. When the ICD 100I needs to be replaced for approaching battery end of life or any other indication, this tangle of insulated conductor segments all tend to have tissue in-growth which makes the surgery difficult as all of these leads must be carefully excised and separated.

FIG. 3A is an electrical schematic simplification of the header 114 and housing 112 shown in FIG. 3. The connector cavities 116, 116', 118, 118' are shown electrically connected by the leadwires through the hermetic seal 124 to the inside of the housing 112 and electrically coupled to the circuit board 126.

Figures 4, 4A:
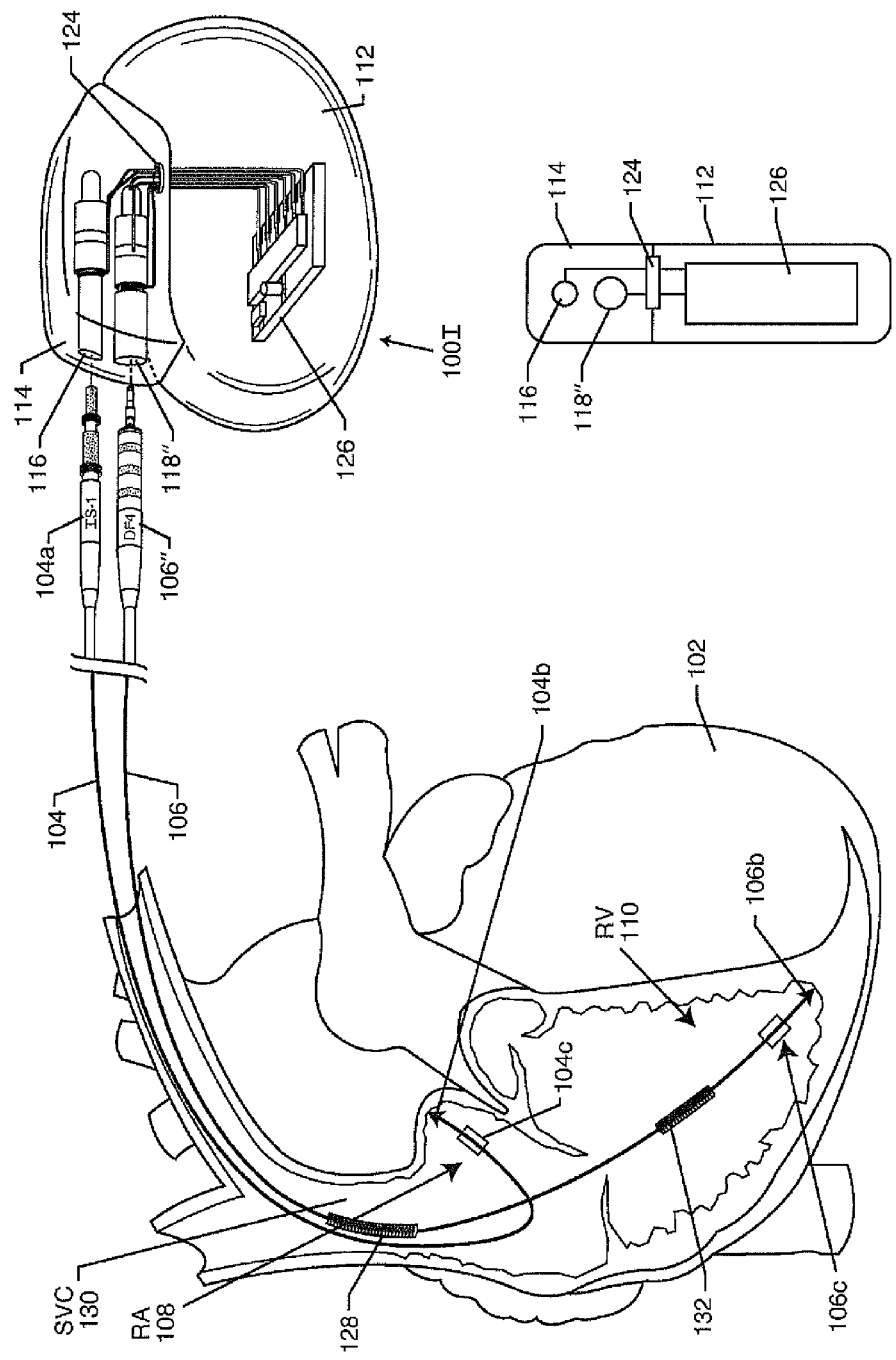
FIG. 4 illustrates a state-of-the-art dual chamber implantable defibrillator similar to FIG. 3 but with the new in-line DF4 quadripolar connector replacing the prior cumbersome trifurcated lead based adaptor.
FIG. 4A illustrates an electrical schematic simplification of the structure of FIG. 4.

FIG. 4 is another prior art cross-section of the human heart 102 again with a dual chamber ICD 100I. As previously illustrated in FIG. 3, the dual chamber ICD 100I has both pacing and high-voltage shocking functions. The electrode placements, both for the high-voltage shocking coils and also the low voltage pace and sense circuits are the same as previously described for FIG. 3. However, in FIG. 4, the defibrillator 100I quadpolar lead 106 incorporates the new state-of-the-art inline quadripolar DF4 proximal lead connector 106" as shown. In this case, there are now only two connector cavities 116 and 118" in the defibrillator 100I header 114. Connector cavity 116 is a low-voltage connector cavity for receipt of the bipolar IS-1 proximal connector 104a. Connector cavity 118" is a DF4 quadripolar connector cavity designed to receive the DF4 proximal connector 106". In this case, there are still two leads 104 and 106 that are routed down into the various chambers of the heart as previously described in FIG. 3. When one considers that excess lead is wound up in the ICD pocket, one can see that the configuration in FIG. 4 is vastly superior to the trifurcated connector 134 as previously illustrated in FIG. 3. The surgical implant procedure is considerably simplified and there is a lot less bulk created in the pacemaker pocket which increases both reliability and patient comfort.

FIG. 4A is an electrical schematic simplification of the header 114 and housing 112 shown in FIG. 4. The connector cavities 116 and 118" are shown electrically connected by the leadwires through the hermetic seal 124 to the inside of the housing 112 and electrically coupled to the circuit board 126.

Figures 5, 5A:
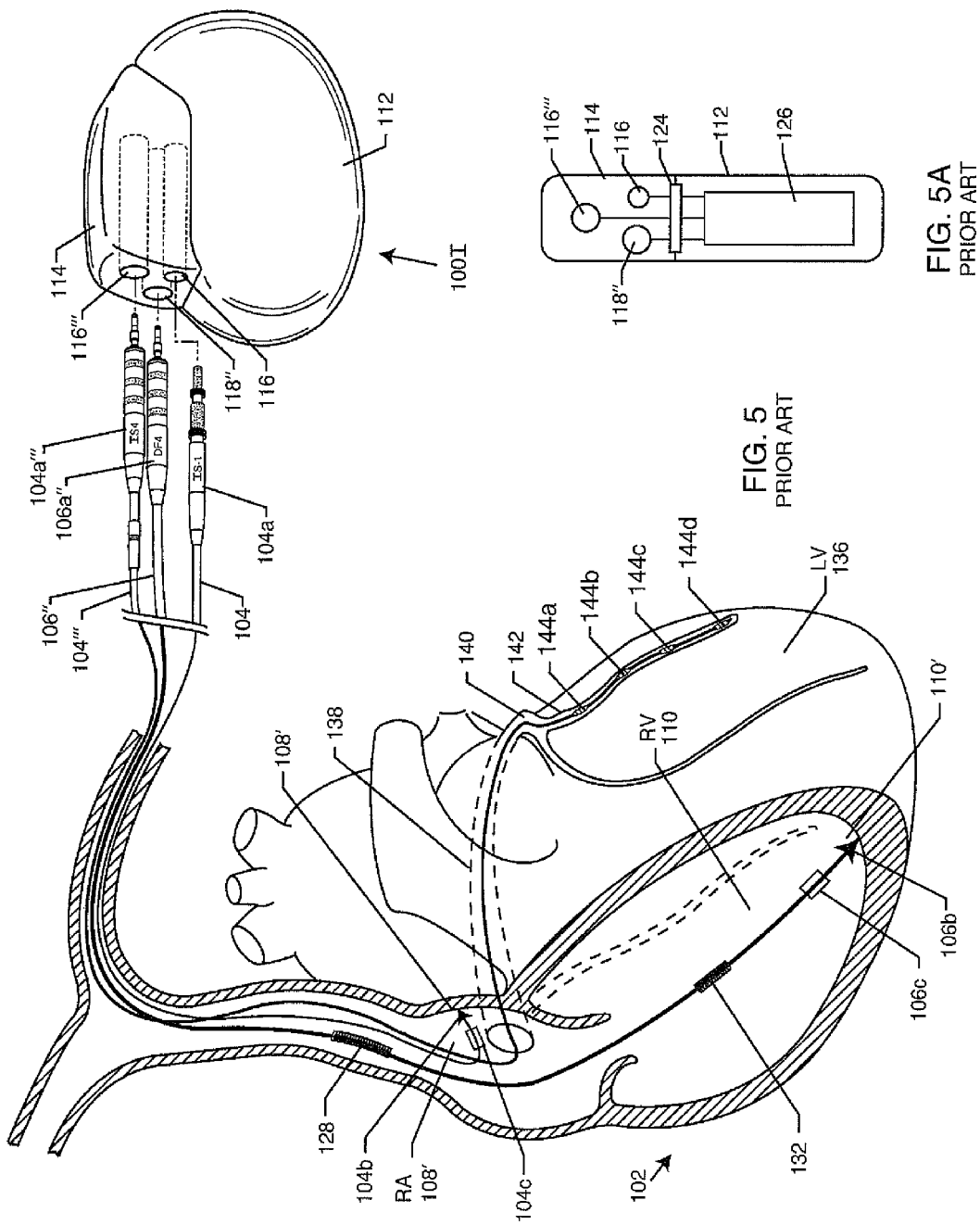
FIG. 5 illustrates a prior art dual chambered ICD that also employs a quadripolar left ventricular lead for simultaneous stimulation of the right and left ventricles, so called cardiac resynchronization therapy or CRT, with both DF4 and IS4 quadripolar leads.
FIG. 5A illustrates an electrical schematic simplification of the structure of FIG. 5.

FIG. 5 is a prior art drawing of a human heart 102 and ICD 100I that is state-of-the-art. This defibrillator system not only has high-voltage shocking and low-voltage pacing functions, but it also has cardiac resynchronization therapy (CRT) capabilities through electrodes placed transvenously into the right atrium 108 and then through the coronary sinus 138 into epicardial veins 140, 142 on the surface of the left ventricle (LV) 136. In this case, there are two types of quadripolar connectors being used at the proximal lead ends. There are three implanted leads 104, 104''' and 106". Lead 104 is a low-voltage bipolar lead which is routed to distal tip 104b and ring 104c electrodes in the right atrial appendage 108'. Lead 106" is a quadripolar low-voltage/high-voltage lead. Lead 106" contains four conductors, two of which are connected to high-voltage shocking coils 128 and 132. There are also two low-voltage conductors in lead 106" which are routed to the distal tip electrode 106b and distal ring electrode 106c in the right ventricular apex 110'. The third lead 104''' is a low voltage four-conductor IS4 or quadripolar lead which is routed transvenously through the coronary sinus 138, the great cardiac vein 140 and into a branch vessel 142 which is part of the epicardial or surface venous system draining blood from the left ventricle 136 back into the right atrium 108. Shown are four electrodes 144a through 144d. The IS4 proximal connector for lead 104''' is plugged into connector cavity 116''' on the header block 114 of the ICD 100I. The DF4 connector 106a" is plugged into connector cavity 118" and the IS-1 proximal connector 104a is plugged into connector cavity 116 as shown.

FIG. 5A is an electrical schematic simplification of the header 114 and housing 112 shown in FIG. 5. The connector cavities 116''', 116 and 118" are shown electrically connected by the leadwires through the hermetic seal 124 to the inside of the housing 112 and electrically coupled to the circuit board 126.

Figure 6:
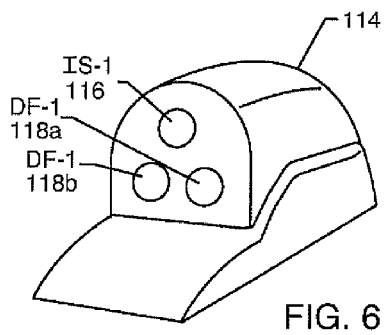
FIG. 6 illustrates the header block of a prior art implantable single chamber defibrillator showing two high-voltage DF-1 connector cavities and a single low-voltage IS-1 connector cavity.

FIG. 6 illustrates a prior art header connector block 114 of a prior art AIMD with two high-voltage connector cavities 118a, 118b which are both DF-1 and a low-voltage bipolar connector cavity 116 in accordance with IS-1. Each high-voltage connector cavity 118a, 118b would be unipolar and routed to a defibrillation shock coil 128, 132 (not shown). The low-voltage connector cavity 116 would be bipolar and routed to a distal tip 104b and ring 104c electrode (not shown).

Figure 7:
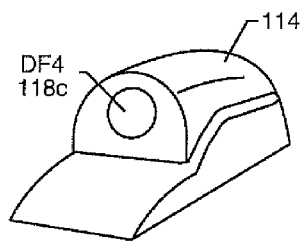
FIG. 7 illustrates how the new quadripolar DF4 connector provides equivalent function to FIG. 6 but with one rather than three primary header connector cavities.

FIG. 7 is exactly the same system illustrated in FIG. 6 except that the three connector cavities have been replaced with a single DF4 quadripolar connector or cavity 118c. In this case, both the high-voltage and the low-voltage functions are all in one DF4 connector.

Figure 8:
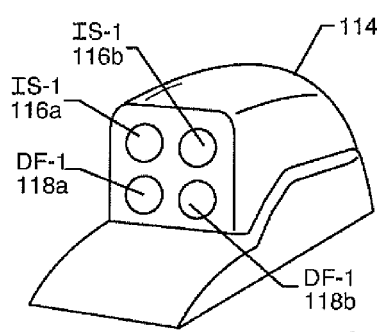
FIG. 8 illustrates a dual chamber defibrillator header with both atrial and ventricle connector cavities where the high-voltage connector cavities are DF-1 and the right ventricular and atrial connector cavities are IS-1.

FIG. 8 is the header 114 of a dual chamber defibrillator with DF-1 high-voltage connector cavities 118a, 118b. In addition, there are two low-voltage connector cavities 116a and 116b. One for a lead to be routed to the right ventricle 110 and the other to the right atrium 108. In this case, there would be two DF-1 connectors and two IS-1 connectors at the proximal ends of the required leads.

Figure 9:
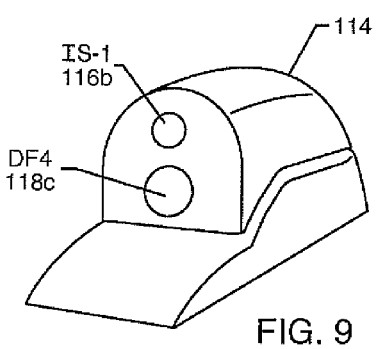
FIG. 9 is the state-of-the-art equivalent to FIG. 8 wherein both DF-1 connector cavities and one IS-1 connector cavity have been replaced by a single inline DF4 quadripolar connector.

FIG. 9 shows how the inline quadripolar DF4 connector 146 can be used to reduce four connector cavities 118a, 118b, 116a and 116b to two cavities 118c and 116b. This is a logical progression from what is described in FIGS. 6 and 7. One connector cavity 118c would be DF4 for streamlined provision of both low voltage ventricular pacing and sensing, and in addition dual coil high voltage defibrillator function. The second connector cavity 116b, would be IS-1 bipolar capable of providing atrial electrical stimulation and sensing.

Figure 10:
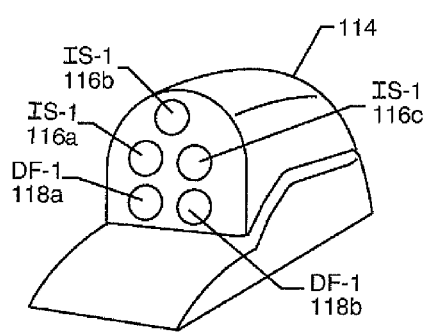
FIG. 10 illustrates a dual chamber defibrillator with CRT capability.

FIG. 10 shows a dual chamber defibrillator primary header 114 with the addition of CRT functions requiring a total of five connector cavities. The two high-voltage connector cavities 118a, 118b are DF-1 and the low voltage connector cavities 116a, 116b and 116c are IS-1 connectors. Required leads and intended functions are identical to what is described in detail above. The additional, fifth low-voltage connector cavity is for receipt of an IS-1 type connector, whereby, a fifth lead would be routed through the venous system into the right atrium 108, the coronary sinus 138 and from there into subepicardial branch coronary veins near the lateral surface of the left ventricle, (see FIG. 5).

Figure 11:
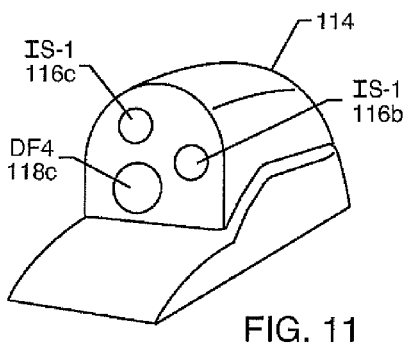
FIG. 11 is the modern equivalent of FIG. 10 showing a DF4 quadripolar connector that replaces the two high voltage DF-1 connector cavities and the one IS-1 connector cavity.

FIG. 11 shows the system of 10 simplified from five to three connector cavities. The DF4 cavity 118c provides for combined dual coil high-voltage functions and the low voltage bipolar pace sense function, all into the newly standardized quadripolar connector. There is still a necessity to have a low-voltage connector cavity 116c for an IS-1 lead to be routed to the left ventricle and also an atrial connector cavity 116b for a second IS-1 lead to be routed to the right atrium.

Figure 12:
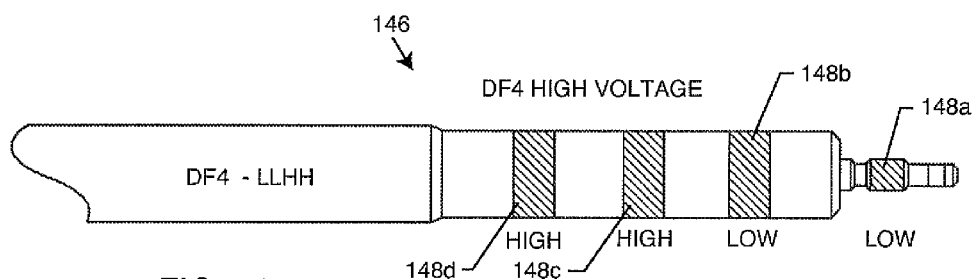
FIG. 12 illustrates an enlarged pictorial view of an embodiment of a proximal end portion of a DF4 high-voltage connector.

FIG. 12 is an enlarged pictorial view of an embodiment of a proximal end portion of a DF4 high-voltage connector 146. As can be seen, at its proximal tip, it has a low-voltage pin electrode connection contact 148a and it also has a low-voltage contact ring 148b next in line. In addition, it has two high-voltage contact rings 148c and 148d. This makes for a four-conductor lead as previously described as lead 106a'' in FIG. 5. This is the same as the DF4 lead 106'' previously shown in FIG. 4.

Figure 13:
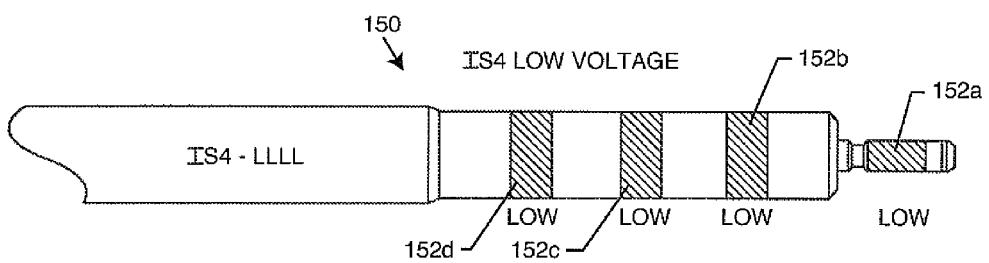
FIG. 13 illustrates an enlarged pictorial view of an embodiment of a proximal end portion of an IS4 low-voltage quadripolar lead connector.

FIG. 13 is an enlarged pictorial view of an embodiment of a proximal end portion of an IS4 low-voltage quadripolar lead connector 150. As illustrated, the connector 150 comprises a low-voltage connector tip 152a and three low-voltage contact rings 152b, 152c and 152d. This is the same as the low-voltage IS4 left ventricular lead 104a''' as previously described in FIG. 5.

Figure 14:
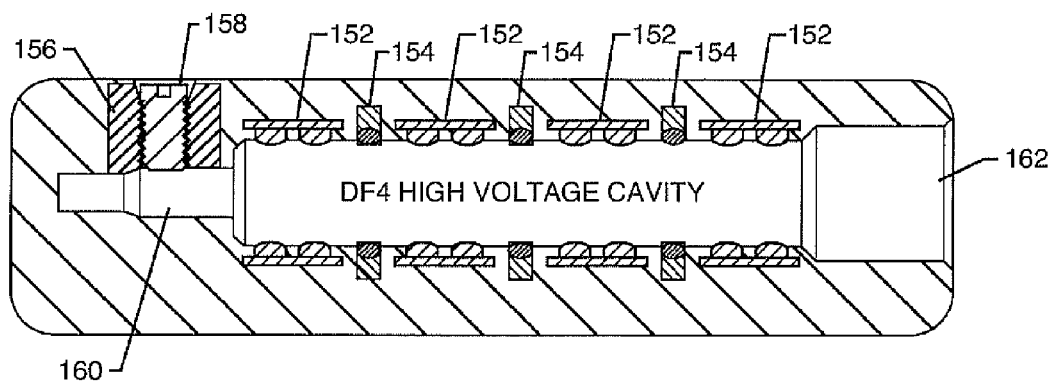
FIG. 14 illustrates an ISO DF4 high voltage cavity.

FIG. 14 illustrates an ISO DF4 high voltage cavity. This is otherwise known as a port in a header block for an AIMD. It has an opening for port 162 to receive the proximal end connector of an implanted lead (not shown). There are multiple seals 152 to prevent ingress of body fluids and moisture. There are electrical contact rings 154 as shown. These contact rings are designed to mate up with corresponding ring contacts of the proximal connector (not shown). There is also a tip area 160 to receive the tip of the connector. Set screw 158 would be firmly seated against the low voltage pin electrode connection contact 148a (not shown). There are leadwires (not shown) attached to connector block 156 and to each of the electrical contact rings 154.

Figure 15:
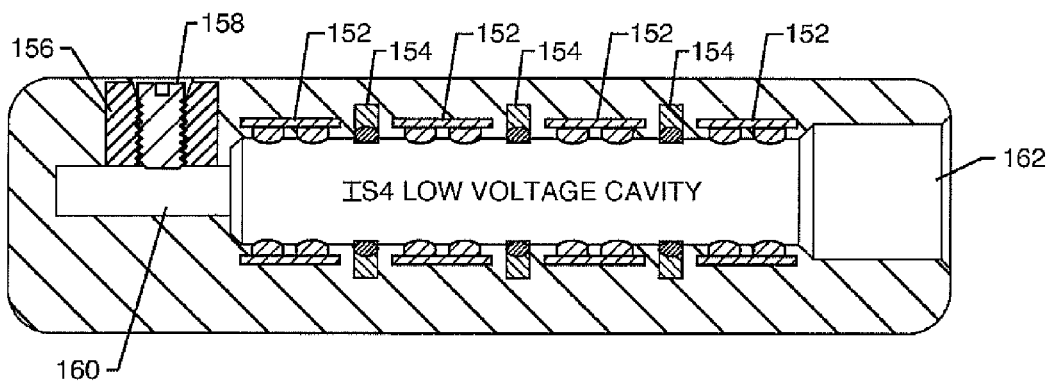
FIG. 15 illustrates an IS4 low voltage cavity which is very similar to FIG. 15.

FIG. 15 is an IS4 low voltage cavity which is very similar to FIG. 15.

Figure 16:
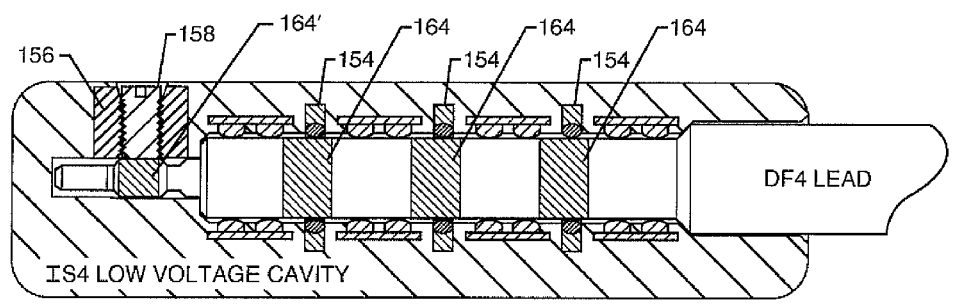
FIG. 16 illustrates an IS4 low voltage cavity with a DF4 proximal connector improperly inserted into it.

FIG. 16 illustrates an IS4 low voltage cavity with a DF4 proximal connector improperly inserted into it; however, it will still work. In the DF4 Standard, a DF4 lead, when inserted into a low voltage cavity, will make proper electrical contact in all four of its points.

Figure 17:
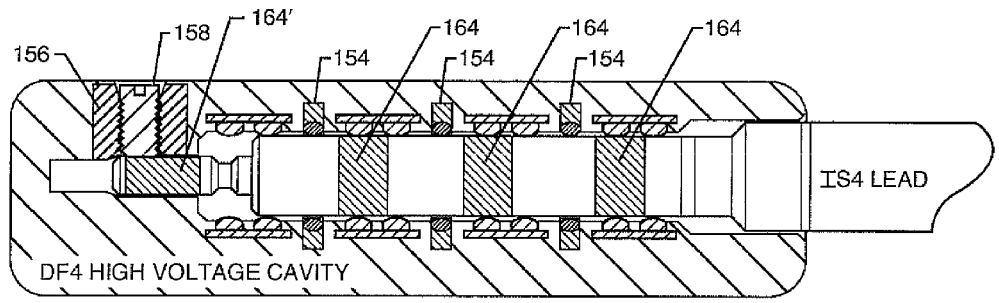
FIG. 17 illustrates a DF4 high voltage cavity with an IS4 lead inadvertently plugged into it.

FIG. 17 illustrates the opposite situation. In this case, we have a DF4 high voltage cavity with an IS4 lead inadvertently plugged into it. This is a highly dangerous situation in that the active implantable medical device, such as an ICD, could inadvertently provide a high voltage pulse to low voltage circuits. This is why the IS4 lead is locked out and will not properly fit into the DF4 high voltage cavity. Referring once again to FIG. 16, one will see that the contact rings 164 all line up and make contact with the corresponding connector ring 154, which are connected to leadwires (not shown). Also, the set screw 158 lines up and makes direct contact with contact ring 164'. Referring once again to FIG. 17, one will see in the locked-out situation, the low voltage IS4 contact rings 164 will not properly line up with the corresponding contacts 154. This provides a safe guard open circuit so that high voltage cannot inadvertently be applied to low voltage electrodes implanted in the heart.

Figure 18:
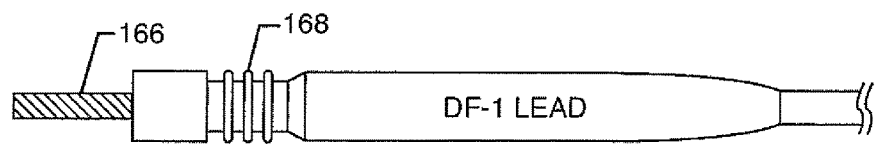
FIG. 18 illustrates a pictorial view of a DF-1 high voltage proximal lead connector.

FIG. 18 is a pictorial view of a DF-1 high voltage proximal lead connector. One will see that it is unipolar and has a tip connector 166.

Figure 19:
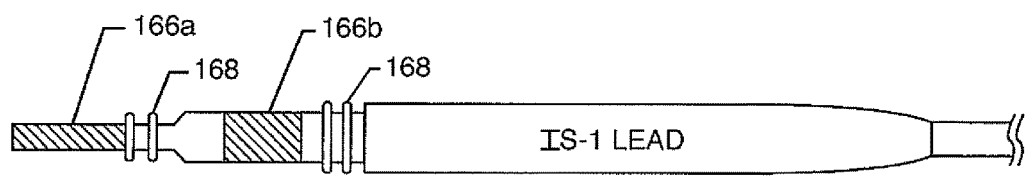
FIG. 19 illustrates an IS-1 bipolar low voltage proximal lead connector.

In contrast, FIG. 19 illustrates an IS-1 bipolar low voltage proximal lead connector, which has a distal tip connector 166a and a ring connector 166b. Referring once again to FIGS. 18 and 19, one can see that there are multiple molded seals 168 to preclude ingress of body fluids or moisture.

Figure 20:
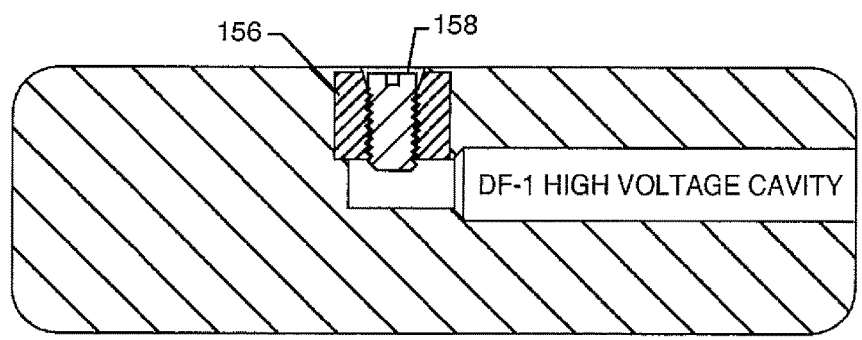
FIG. 20 illustrates a sectional view of a DF-1 high voltage connector cavity that is ready to receive the proximal connector previously illustrated in FIG. 18.

FIG. 20 is a sectional view of a DF-1 high voltage connector cavity that is ready to receive the proximal connector previously illustrated in FIG. 18. It is unipolar and is designed to be held in place by set screw 158.

Figure 21:
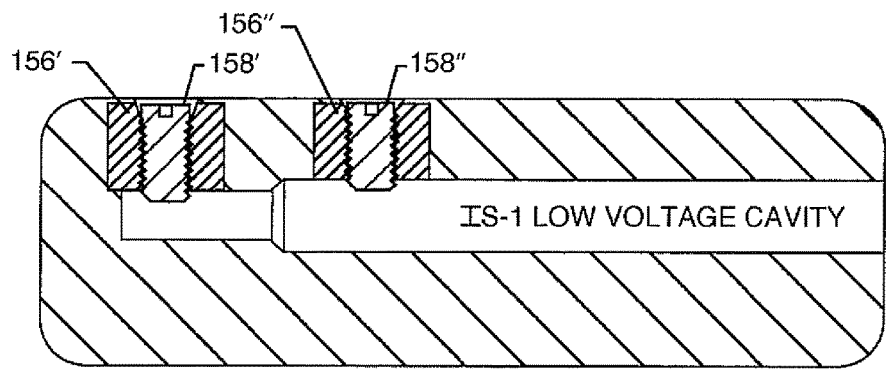
FIG. 21 illustrates an IS-1 low voltage connector cavity which is ready to receive the proximal IS-1 connector previously illustrated in FIG. 19.

FIG. 21 is very similar to FIG. 20 and illustrates an IS-1 low voltage connector cavity which is ready to receive the proximal IS-1 connector previously illustrated in FIG. 19. In this case, there are two set screws 158' and 158" which both firmly affix the lead connector in place and also make electrical contact to contact points 166a and 166b.

Figure 22:
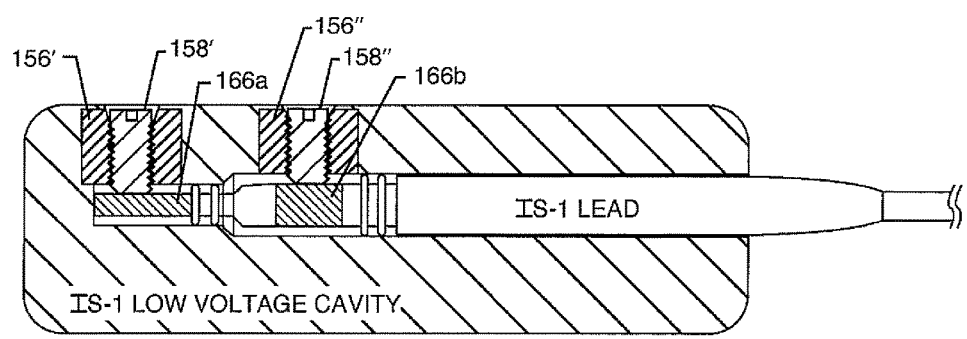
FIG. 22 illustrates the IS-1 proximal lead connector previously shown in FIG. 19 and inserted into the IS-1 low voltage connector cavity previously illustrated in FIG. 21.

FIG. 22 illustrates the IS-1 proximal lead connector previously shown in FIG. 19 and inserted into the IS-1 low voltage connector cavity previously illustrated in FIG. 21. One can see that set screws 158' and 158" make both an electrical and a mechanical connection to contacts 166a and 166b.

Figure 23:
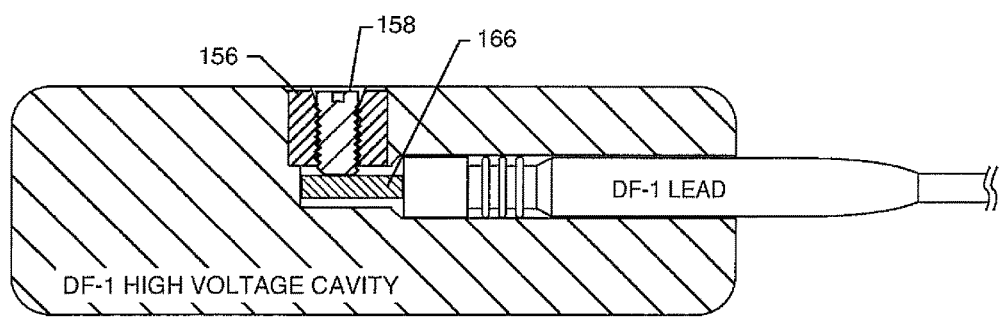
FIG. 23 illustrates the DF-1 proximal connector previously illustrated in FIG. 18 inserted into the DF-1 high voltage connector cavity previously illustrated in FIG. 20.

FIG. 23 is very similar to FIG. 22 and shows the DF-1 proximal connector previously illustrated in FIG. 18 inserted into the DF-1 high voltage connector cavity previously illustrated in FIG. 20. Again, set screw 158 makes mechanical and electrical connection to the contact area 166.

Figures 24, 24A:
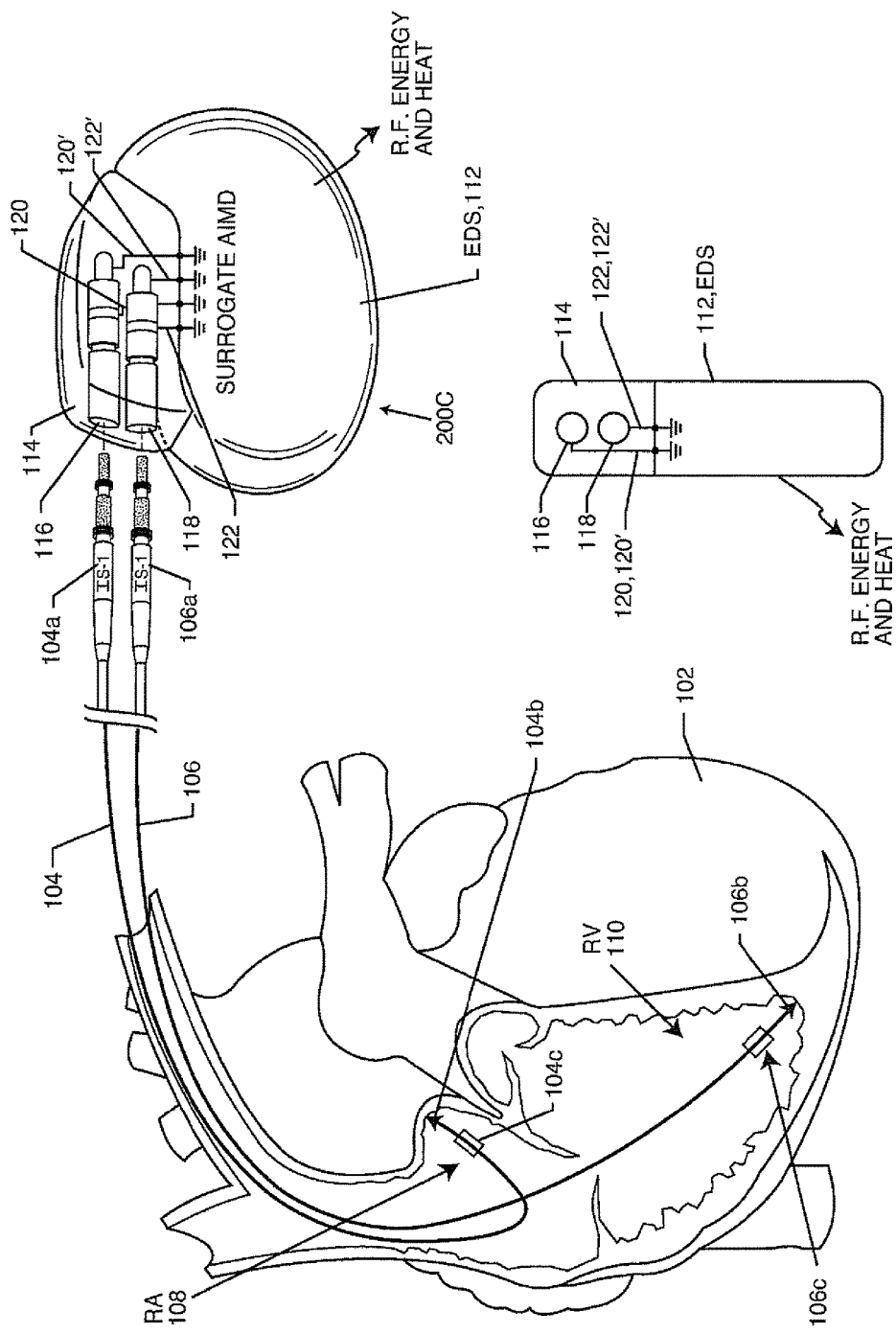
FIG. 24 illustrates a surrogate AIMD of the present invention.
FIG. 24A illustrates an end view of the surrogate AIMD previously illustrated in FIG. 24.

FIG. 24 shows a surrogate AIMD 200C of the present invention with leads 104 and 106 directed into human heart 102. This is very similar to the system as previously described in FIG. 2. In this case, the pacemaker 100C previously described in FIG. 2 has been surgically removed and the leads 104 and 106 have been unplugged. Proximal connectors 104a and 106a are therefore left in the now empty pacemaker pocket. A surrogate AIMD 200C, in accordance with the present invention, is inserted into the now empty tissue pocket and the proximal plugs 104a and 106a are plugged into ports 116 and 118 of the surrogate AIMD 200C. The surrogate AIMD 200C has all of its connector port contact rings grounded to the AIMD housing. Grounding all of the lead conductors (in this case, four) to the AIMD housing 112, the AIMD housing becomes an energy dissipating surface or EDS. As previously described, MRI RF energy can be induced along the length of the lead conductors and bipolar leads 104 and 106. It is undesirable to have this energy flow into the distal electrodes 104b, 104c, 106b or 106c. It has been shown the excessive current flow or heat rise at the myocardial interface can damage sensitive myocardial tissue and can even increase pacing capture threshold (PCT), can cause complete lack of pacing or even cause dangerous lesions or perforations which can be life-threatening. The surrogate AIMD has a relatively large surface area when compared to the relatively small surface area of the electrodes 104b, 104c, 106b or 106c. By grounding all four of the lead conductors directly to the surrogate AIMD housing 112, a great deal of MRI RF-induced energy is pulled from the leads and is redirected to the AIMD housing where it is dissipated as a small amount of temperature rise or RF energy. By dissipating the RF energy over a relatively large surface area, a great deal of this energy can be dissipated without significant temperature rise. Also of Importance, is the fact that the RF energy is being redirected and dissipated in the pacemaker pocket. This pocket is generally either subcutaneous, in a fat layer, in muscle or underneath muscle. When compared to myocardial tissue, the pockets tissues are far less sensitive to thermal damage. The present invention, of course, applies to all types of AIMDs as previously described in FIG. 1. For example, if the AIMD is a deep brain stimulator, previously illustrated in FIG. 1 as 100B, it is even more important that the distal electrodes not overheat. This is because deep brain tissue is much more sensitive to thermal injury as compared to the myocardial tissue of the human heart.

FIG. 24A is an end view of the surrogate AIMD 200C previously illustrated in FIG. 24. Shown is the end view of the two header block 114 IS-1 connector ports 116 and 118. One can see that bipolar lead wires 120 and 120' are connected from the header port contacts 116 directly to the AIMD housing 112 where the ground symbols are shown. In a likewise fashion, leadwires 122 and 122' are grounded to the connector port contacts 118 directly to the AIMD housing 112. As will be later illustrated and described in FIG. 39, there is an alternative to directly grounding the lead conductors to the AIMD housing. However, direct ground attachment is very effective and is the preferred embodiment. One reason directly grounding the leadwires as illustrated in FIG. 24A is preferred is that no hermetic terminal is required for the surrogate AIMD. This reduces the cost of the surrogate AIMD significantly. The other thing that reduces the cost of the surrogate AIMD is that it has no internal battery, electronic circuits or the like. It's only purpose is to provide a relatively large surface area to dissipate energy in the pocket which will enable the patient to safely undergo an MRI without the need for the patient to undergo extraction of leads 104 and 106. Lead extraction is a difficult and lengthy procedure that has a number of significant risks associated with it. When leads are implanted for long periods of time, they tend to be overgrown by tissues.

Figure 24B:
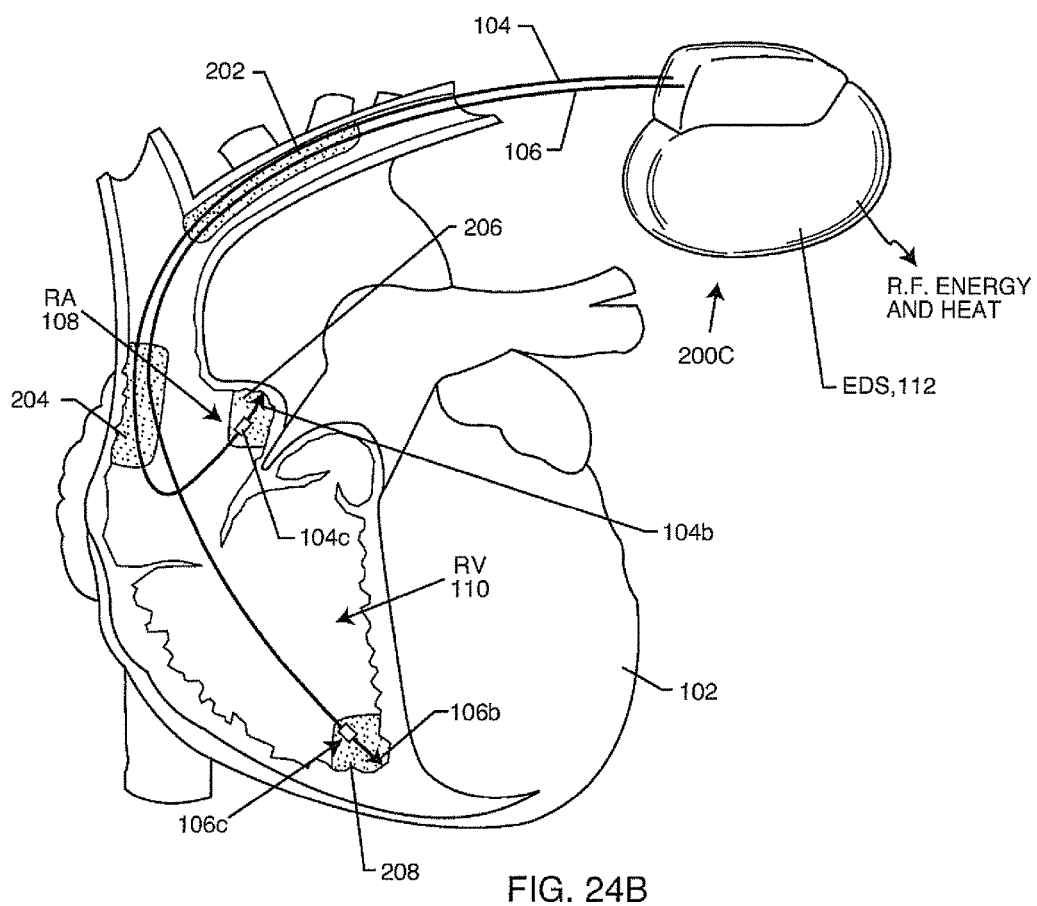
FIG. 24B illustrates tissue overgrowths and encapsulated implanted leads.

Referring to FIG. 24B, the shaded areas 202, 204, 206, 208 show where tissue typically overgrows and encapsulates the implanted leads 104 and 106. In other words, one cannot simply pull on the proximal end of the lead and gently pull it out of the heart after it's been implanted for a long time. It takes special extraction procedures, using cutting blades and lasers, to extract the leads which usually come out with a great amount of tissue attached to them. Also there is a significant risk of vessel wall perforation, infection and the like. Accordingly, those skilled in the art will realize that extracting implanted leads is a difficult and dangerous procedure. It is a key feature of the present invention that the surrogate AIMD allows the preexisting leads to remain in place and safely undergo an MRI scan. After the MRI scan is over, the pacemaker pocket is reopened and the original or a new functioning pacemaker can be put back in. If not very much battery life had been used, it is likely the surgeon would re-implant the original pacemaker. If the pacemaker was near its end of life or due for battery replacement, then it becomes highly likely that a new pacemaker would be plugged in to the existing leads 104 and 106.

Cardiac pacemakers have been used to illustrate both the difficulty of explanting pre-existing leads and the ease by which a surrogate AIMD could be installed to enable the MRI procedure. As previously mentioned, the surrogate AIMD provides a high energy dissipation surface to remove unwanted MRI induced energy from the lead. It is important that the surrogate AIMD be of relatively low cost compared to an actual functioning AIMD. As previously mentioned the surrogate AIMD has no battery, no internal electronic circuits and not even a hermetic seal 124 that has been previously described. The surrogate AIMD is therefore limited to the can, the header block and the header block connector ports 116 and 118. In general, the surrogate AIMD will be removed and discarded after the MRI imaging procedures are completed. It will be possible, in certain embodiments, that the surrogate AIMD could be desterilized and used again.

So far, a cardiac pacemaker has been used to illustrate the principles of the present invention. It will be appreciated that lead extraction is even more difficult for other types of AIMDs, such as cochlear implants, deep brain stimulators, spinal cord stimulators and the like. In each of these cases there is a AIMD housing with a casing and then implanted leads. For example, in a cochlear implant, the implanted leads are literally shoved up into the cochlear area where they become overgrown when in contact with auditory nerves. Ripping that cochlear implant bundle back out literally would destroy the nerves that are associated with it. In other words, lead extraction, in that case, is simply not possible. Deep brain stimulators and spinal cord stimulators and other types of neurostimulators present similar challenges. For example, once a deep brain electrode is placed and it becomes overgrown by deep brain tissue, one can see that extracting it would it cause great trauma to surrounding brain tissues. Then one would have to go through a re-implantation procedure, which would cause even more brain trauma. Accordingly, in these cases, the surrogate AIMD of the present invention becomes very important. One only need remove the AIMD housing and replace it with the surrogate housing to safely perform procedures on all of the aforementioned structures and those devices as previously described in FIG. 1.

Figures 25, 25A:
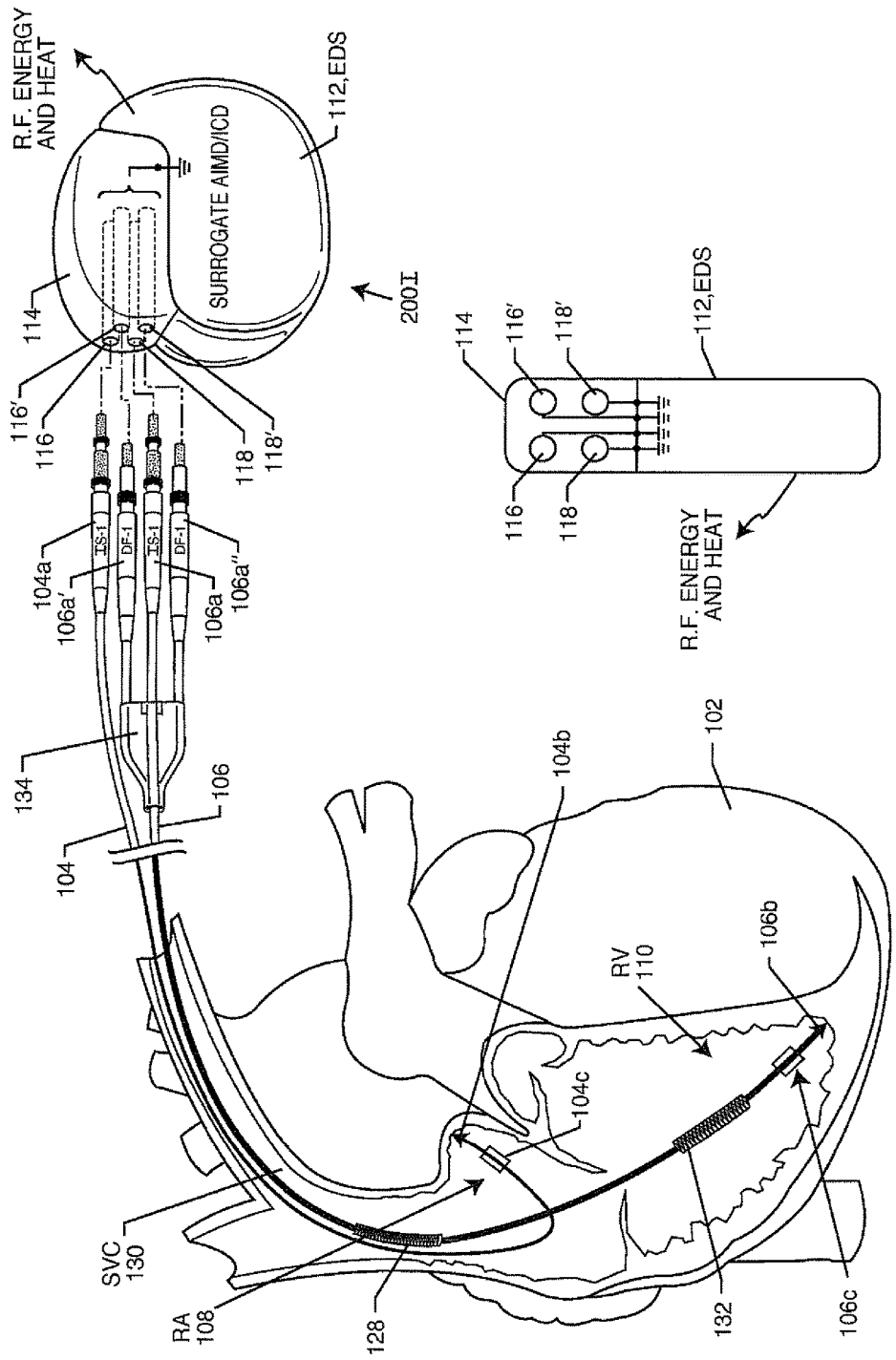
FIG. 25 illustrates a surrogate ICD very similar to the system previously described in FIG. 3.
FIG. 25A illustrates an end view of the ICD of FIG. 25.

FIG. 25 illustrates a surrogate ICD 200I very similar to the system previously described in FIG. 3. There are four proximal connectors 104a, 106a', 106a and 106a". In this case, the surrogate AIMD or surrogate implantable cardioverter defibrillator has four ports 116, 116', 118 and 118'. All of the electrical connectors of these four ports are grounded to the AIMD housing in accordance with the present invention.

FIG. 25A is an end view of the ICD 200I of FIG. 25. This illustrates that all of the leadwires of all of the ports are grounded to the AIMD housing in accordance with the present invention. It should also be noted that in FIG. 25A there is no longer the need for the hermetic seal 124 previously described in FIG. 3A.

FIG. 26 shows a surrogate ICD which is based on previous FIG. 4. In this case, the ICD 100I has been removed from the device pocket and is replaced by surrogate AIMD 200I to enable an MRI procedure. There is a relatively simple medical procedure to make a small incision under local anesthetics on an outpatient basis and remove the AIMD 100I. It can then be placed in a sterile container to be reused at a later time. The sterile surrogate AIMD is then placed into the pocket and plugged into the proximal leadwire connectors 104a and 106". The pocket is temporarily closed by Sterl-Strip™, Tegaderm™ film, tape, adhesives or the like. There is no need to really stitch it closed at this time. The patient then goes and has their MRI procedure and then comes back where again a simple surgical procedure is performed. In this case, the Steri-Strips or other bandages will be removed, the surrogate ICD will be removed and then replaced by either the previous device or a new device depending upon battery condition.

FIG. 26A is an end view of the surrogate ICD 200I previously described in FIG. 26. It shows that all of the context of both the IS-1 and the DF4 ports 116 and 118" have been grounded directly to the ICD housing 112. In accordance to the present invention, the ICD housing 112 becomes an RF energy dissipating surface.

FIG. 27 illustrates a surrogate CRT-D (cardiac resynchronization therapy-defibrillator) and both ventricular electrodes previously described in FIG. 5. This device has dual chamber bipolar pacing capabilities, defibrillation capabilities and left ventricular pacing capabilities to treat conditions such as congestive heart failure. In accordance with the present invention, three ports are provided in the surrogate CRT-D device 200I'. These ports are 116''', 118'' and 116. In accordance with the present invention, the electrical contacts of all of these ports have been connected directly to the device housing 112.

FIG. 27A is an end view of the device taken directly from FIG. 27 and illustrates that all three ports IS4 and DF4 and IS-1 have been directly grounded to the device housing 112 which becomes an energy dissipating surface.

Figure 28A:
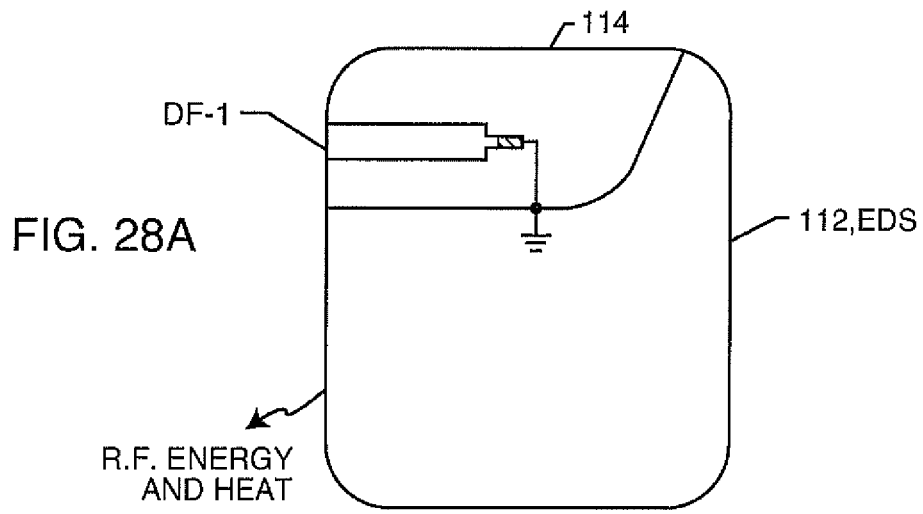
FIG. 28A illustrates a schematic electrical diagram of a DF-1 port of the surrogate AIMD.
Figure 28B:
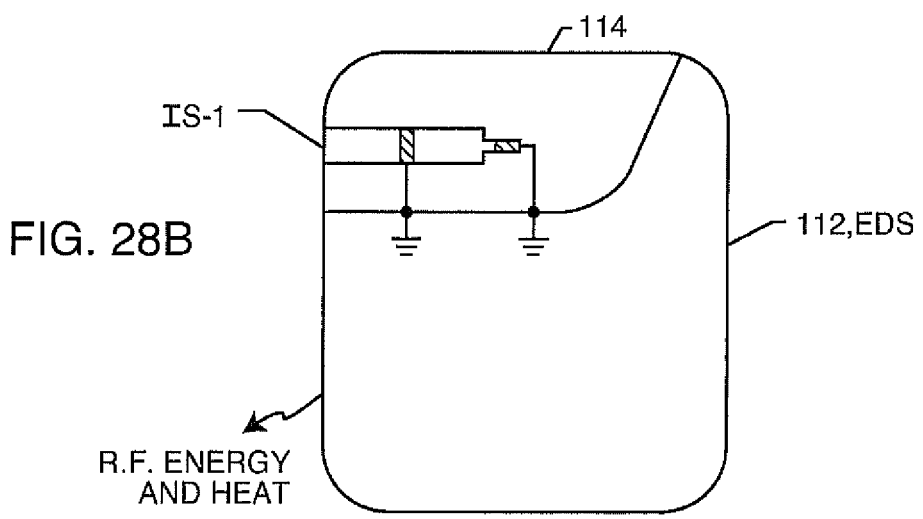
FIG. 28B illustrates a schematic electrical diagram of an IS-1 port of the surrogate AIMD.
Figure 28C:
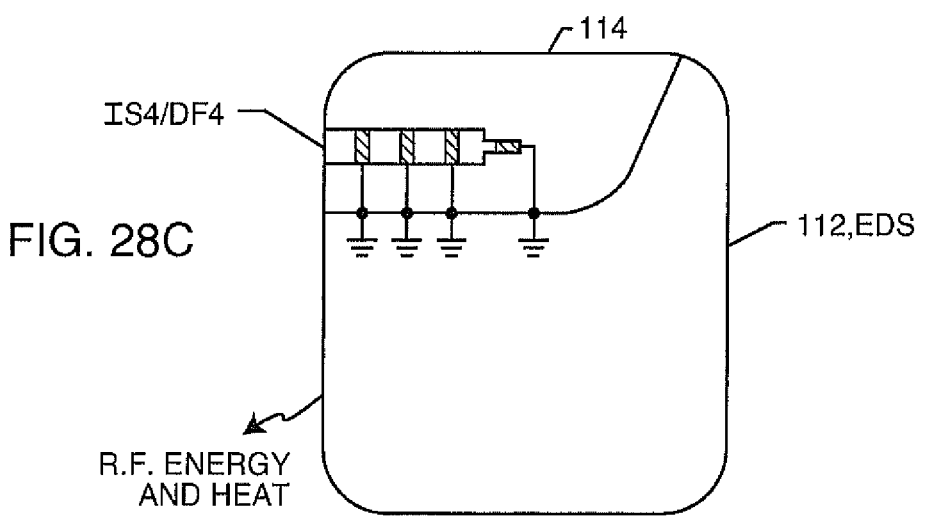
FIG. 28C illustrates a schematic electrical diagram of an IS4/DF4 port of the surrogate AIMD.

FIGS. 28A, 28B and 28C show schematic electrical diagrams inside the header block 114 which illustrates how one would ground a DF-1, an IS-1 or an IS4 or DF4 port of the surrogate AIMD of the present invention. Referring back to FIGS. 24, 25, 26 and 27, one sees just a few illustrative examples of the types of cardiac device lead and connector port systems. It will be obvious to those skilled in the art and experienced in the business side of the industry that inventorying surrogate AIMDs for each unique lead configuration would be very costly. Accordingly, a preferred embodiment of the present invention would be a single surrogate AIMD with a larger number of connector ports such that any combination of IS-1, DF-1, IS4, DF4 proximal pre-existing leads could all be plugged into the surrogate AIMD. It is not even necessary that all of the ports of a surrogate AIMD be used. It is only implanted temporarily therefore; there is really no concern with bacterial contamination or other issues with unused ports. Even if there were, silicone plugs could be placed into the unused ports such that body fluids would not penetrate.

Figure 29:
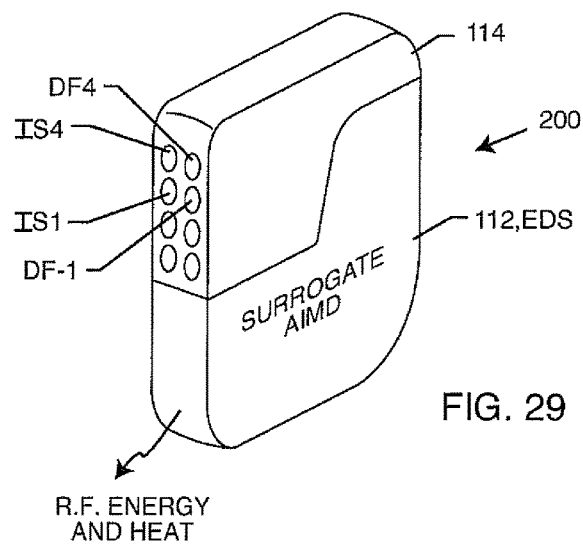
FIG. 29 illustrates a general purpose surrogate device 200 including any combination of IS4, DF4, IS-1 or DF-1 ports.

FIG. 29 illustrates such a general purpose surrogate device 200, which in this case, has eight ports which can consist of any combination of IS4, DF4, IS-1 or DF-1.

Figure 30:
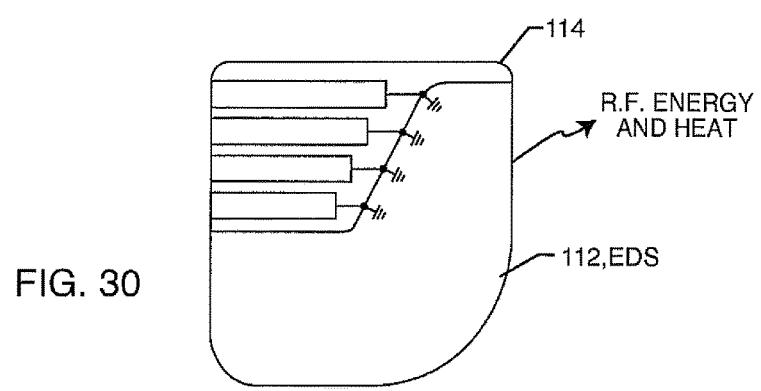
FIG. 30 illustrates the general purpose surrogate AIMD previously illustrated in FIG. 29.

FIG. 30 illustrates the general purpose surrogate AIMD 200 of the present invention previously illustrated in FIG. 29 illustrating that every one of the contact rings and pins of every one of the connectors has been grounded. It is also a feature of the present invention that the surrogate device does not have to have DF4 ports. This is because an IS4 port will receive and make proper electrical connection with both an IS4 proximal plug and a DF4 proximal plug (the opposite is not true). Neurostimulators and cochlear implants, in general, use different types of contacts and connector systems. Accordingly, a surrogate AIMD with the appropriate ports would be provided for those. It will be appreciated that for illustrative purposes, cardiac applications have been illustrated herein in great detail. For neurostimulator applications, or any of the other types of AIMDs described in FIG. 1, it will be appreciated that those might have different types of proximal plugs and connector ports. The present invention applies to all other such applications.

Figure 31:
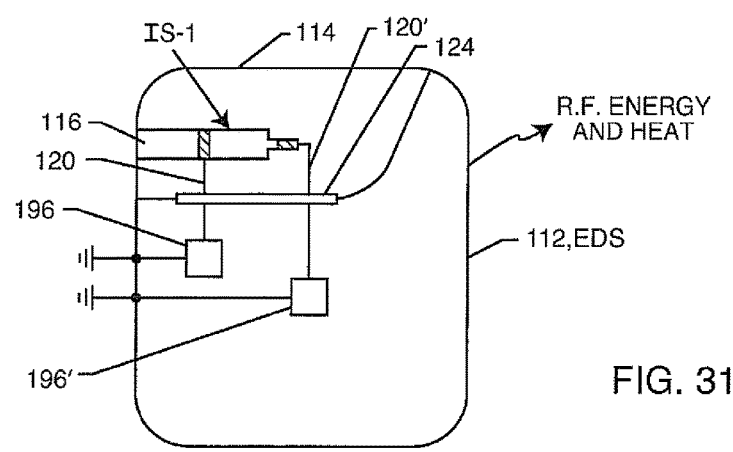
FIG. 31 illustrates a general surrogate AIMD now with a hermetic seal.

FIG. 31 is a general surrogate AIMD of the present invention, but in this case, it has a hermetic seal 124 that's been added. By purposes of illustration, an IS-1 connector port 116 as illustrated, which is bipolar and has a contact ring and a tip ring connection. Leadwires 120 and 120' are routed from these port contacts through the hermetic terminal 124 in non-conductive relation with the AIMD housing 112 and are routed to RF energy diverters 196 and 196'. The diverters contain electronic circuits which are in turn grounded to the EDS housing 112 as shown. Again, only one port 116 is shown for simplicity. For a general cardiac AIMD, there would be a number of ports as previously shown, for example, in FIG. 29 and all of the leadwires of all of these ports would be routed through a hermetic terminal 124 and in turn, each one routed to a diverter 196.

Figure 32:
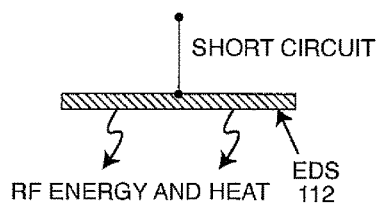
FIG. 32 illustrates an electrical schematic of the short circuit or grounding of the lead conductor to the housing.

FIG. 32 is an electrical schematic of the short circuit or grounding of the ports to the housing 112.

Figure 33:
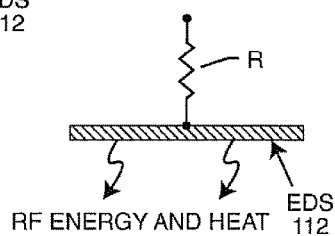
FIG. 33 illustrates that the short circuit will have an inherent resistance R.

FIG. 33 illustrates that the short circuit will have an inherent resistance R.

Figure 34:
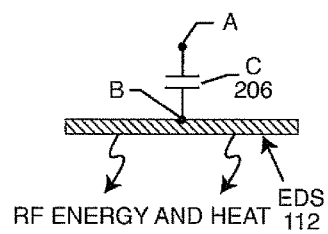
FIG. 34 illustrates that the diverter elements may be a capacitor.

FIG. 34 illustrates that the diverter elements may be a capacitor 206. In this case, an ideal capacitor element is as shown, meaning that it has no inductance and no resistance. A capacitor is an ideal frequency variable diverter because at high frequencies, such at MRI RF-pulsed frequencies, it will tend to look like a very low impedance for a short circuit.

Figure 35:
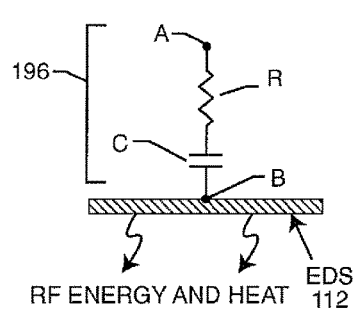
FIG. 35 illustrates one type of frequency variable diverter as previously illustrated in FIG. 31.

FIG. 35 is one type of frequency variable diverter 196 as previously illustrated in FIG. 31. In this case, there is a capacitor C. The resistance R can be a discrete resistor or it can be the inherent resistance of the capacitor which is also known as the capacitor's equivalent series resistance or ESR. At low frequency, the capacitor C as previously illustrated in FIG. 34, will look like a very high impedance. In face, at biological frequencies below one to two kilohertz, the capacitor C will look desirably like an open circuit. However, at high frequency, the capacitor C will tend to look like a short circuit and draw induced MRI RF energy from the lead where it is diverted to the AIMD housing 112 as an energy dissipating surface. These implanted leads are usually coiled and tend to look inductive as a source impedance. In order to transfer maximum energy to the energy dissipating surface, a capacitive element is desirable so that the +jΩL term will be canceled by the −jΩC term.

Figure 36:
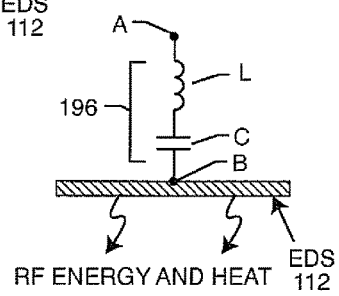
FIG. 36 illustrates a different type of diverter known as an L-C trap.

FIG. 36 illustrates a different type of diverter known as an L-C trap. In this case, the inductor element L and the capacitor element C are designed to be resonant at one or more MRI RF-pulsed frequencies. At resonance, an L-C trap tends to look like a short circuit. Accordingly, in accordance with the present invention, MRI induced RF energy on the implanted lead, is shorted to the EDS surface 112.

Figure 37:
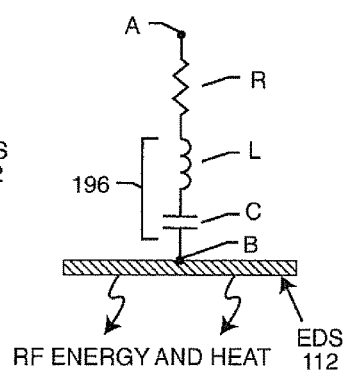
FIG. 37 illustrates the addition of a resistor to the L-C trap of FIG. 36.

FIG. 37 illustrates the addition of a resistor R to the L-C trap of FIG. 36. The resistive element R is important so one can control the Q and the bandwidth of the L-C trap at resonance. One of these principles is more thoroughly described in U.S. Pat. No. 7,966,075, the contents of which are incorporated herein by reference.

FIGS. 38A through 38F are end views of the connector port, which are very similar to that previously described in FIG. 24A. One will appreciate that there can be any number of ports and that two are shown just for simplicity. Referring to FIG. 38A, one can see that there is a thickened and highly thermally conductive and electrically conductive area 210. This is in order to increase thermal conductivity and thermal mass and to also increase the amount of RF dissipation into the energy dissipating surface 112.

FIG. 38B is very similar to FIG. 38A except that in this case, the surrogate AIMD housing has been filled with a gel, a liquid, a paste or the like 212. This material would have a very high thermal conductivity. A preferred embodiment would have high electrical conductivity as well. This is to promote heat dissipation over the entire AIMD housing 112. Material 212 could also be phase change material, which would absorb a significant amount of energy before it increased in temperature.

FIG. 38C is very similar to FIG. 38A except in this case, the EDS housing 112 includes a number of heat dissipating fins 214. In this case, the fins are oriented vertically as shown.

FIG. 38D is very similar to FIG. 38C except that in this case the heat dissipating fins 214 have been oriented horizontally. It will be appreciated that the fins could appear on both sides or even all around the AIMD housing 112.

FIG. 38E is very similar to FIG. 38A. In this case, the energy dissipating surface 112 has been interlocked with a flexible material, such as a silicone or the like, which has thermally-conductive additives 216. This allows the surrogate AIMD to closely conform to the tissue surfaces that are inside of the pocket area.

FIG. 38F is very similar to FIG. 38A except that in this case the surrogate AIMD housing 112 is a solid block of metal which would be highly electrically conductive and also highly thermally conductive. It has another advantage in that it would have a very high thermal mass, meaning that it would be very slow to heat up.

Figure 39:
FIG. 39 illustrates an enlarged view of any of the energy dissipating surfaces.

FIG. 39 is an enlarged view of any of the energy dissipating surfaces 220 of the AIMD housing 112. Shown is a convoluted surface such that the surface area of the energy dissipating surfaces increases. This aids in both dissipation of RF energy and in dissipation of thermal energy. Major advantages of the convoluted surface as illustrated in FIG. 39 is that it will also increase the MRI induced RF energy that is transferred and dissipated from an implanted lead 104 or 106 (not shown).

Figure 40:
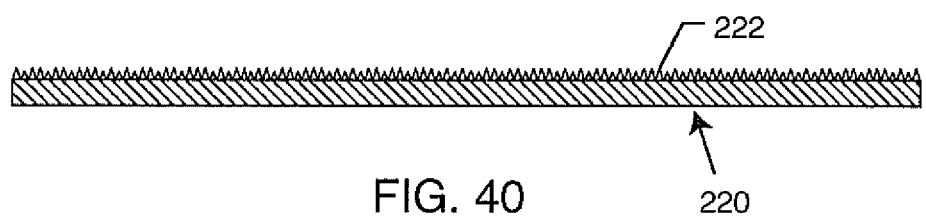
FIG. 40 illustrates a roughened surface providing additional energy dissipation area.

FIG. 40 is similar to FIG. 39 except that instead of convolutions, a roughened surface 222 provides additional energy dissipation area. The energy dissipating surface area 220 has been roughened 222 to create a high surface area, through, for example, plasma etching, sputtering, chemical etching, or the like. A high surface area can also be accomplished by porous coating deposits utilizing physical vapor deposition, chemical vapor deposition or electron beam deposition processes. Such porous coating deposits can include fractal coatings, metal nitrides, titanium nitrides, metal oxides, metal carbides, or virtually anything that would provide a high surface or porous substrate. In addition, electrochemical deposition of a porous coating, such as iridium-oxide, can also be utilized, as well as nucleate high surface area morphological structures such as columnar, titanium-nitride or iridium-oxide. Any of these types of surface conditionings can greatly increase the energy dissipating surface area.

Figure 41:
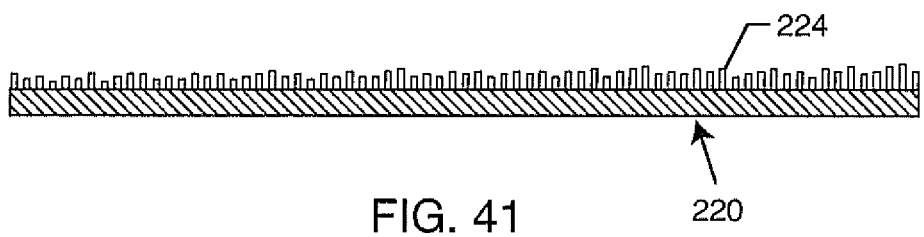
FIG. 41 illustrates the use of carbon nanotubes or fractal coatings to increase the surface area and energy dissipation.

FIG. 41, which is similar to FIG. 40, illustrates the use of carbon nanotubes or fractal coatings 224 to increase the surface area and therefore the energy dissipation.

Figure 42:
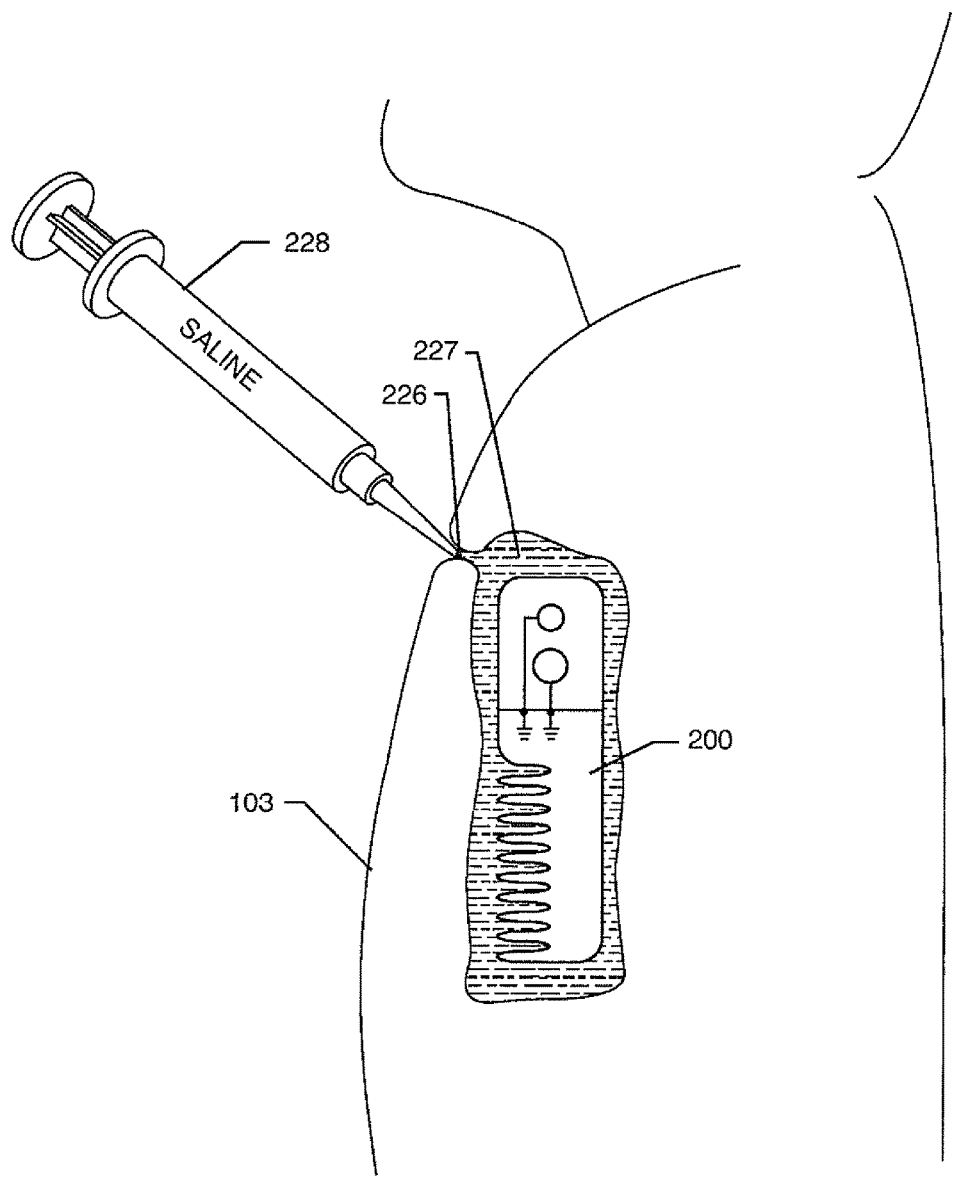
FIG. 42 illustrates the side view of a patient with an enlarged pectoral pocket to receive a surrogate AIMD of the present invention.

FIG. 42 illustrates the side view of a patient with an enlarged pectoral pocket 227 to receive a surrogate AIMD 200 of the present invention. As previously described, a small incision 226 is made to remove the active AIMD, which is then replaced with the surrogate AIMD 200. After the pre-existing leads (not shown) are plugged into the surrogate device, it is then filled with sterile saline solution using a syringe 228. The purpose of the sterile saline solution is so that an intimate contact is made all around any of the previously described energy dissipating surfaces of the present invention. The sterile saline will be both electrically conductive at RF frequencies and also highly thermally conductive. Importantly, it will mate closely with any of the high surface embodiments previously illustrated. After the saline is injected and literally fills all voids in the pocket 227, various types of pre-existing medical tapes are used to close the incision. Closing the incision with this temporary tape ensures that the saline will not leak out and that over-bandages are placed with suitable antibiotics, such that the wound may not be infected. A patient may now go to the radiology suite to receive an MRI. Upon returning from the MRI, the tape is removed and the surrogate AIMD is pulled out of the pocket and the excess saline is easily suctioned out. As previously described, the previous AIMD or a new AIMD would then be inserted and plugged into the pre-existing leads.

Figure 43:
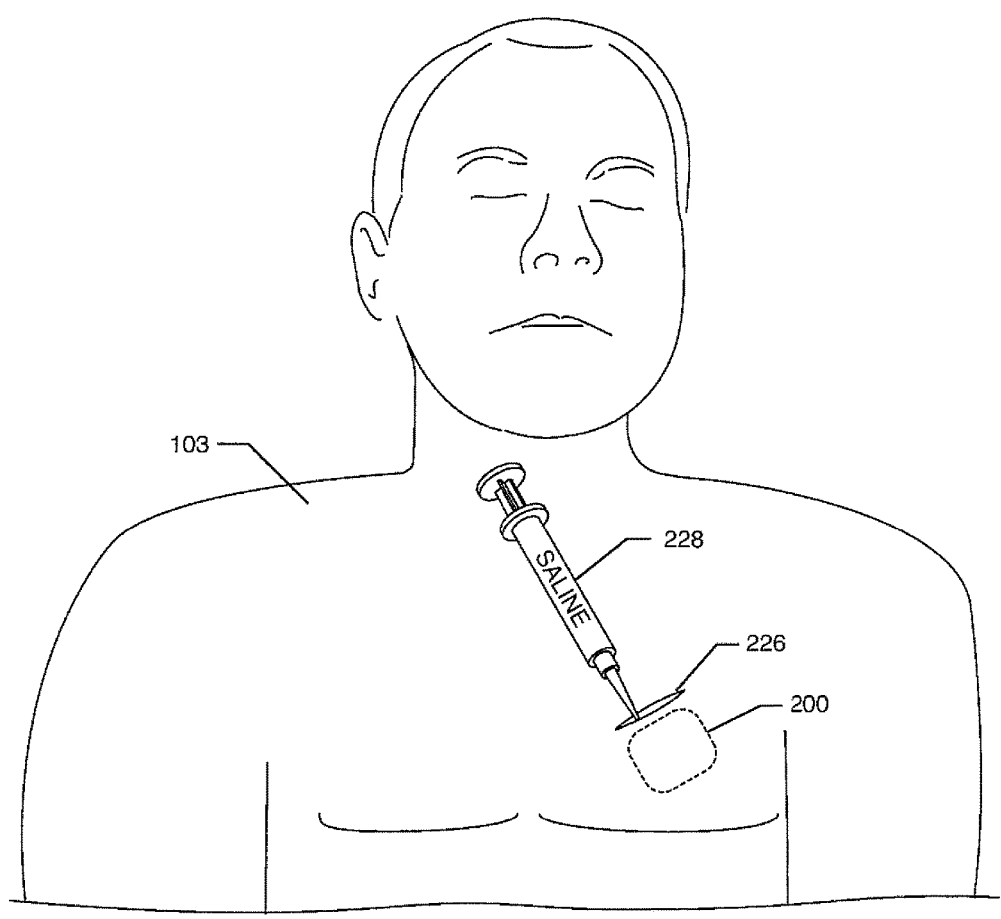
FIG. 43 illustrates the front view taken from FIG. 42 showing the incision, the surrogate AIMD and the injection of saline to fill the pocket.

FIG. 43 illustrates the front view taken from FIG. 42 showing the incision 226, the surrogate AIMD 200 and the injection of saline to fill the pocket 228. The closure tapes are not shown.

Figure 44:
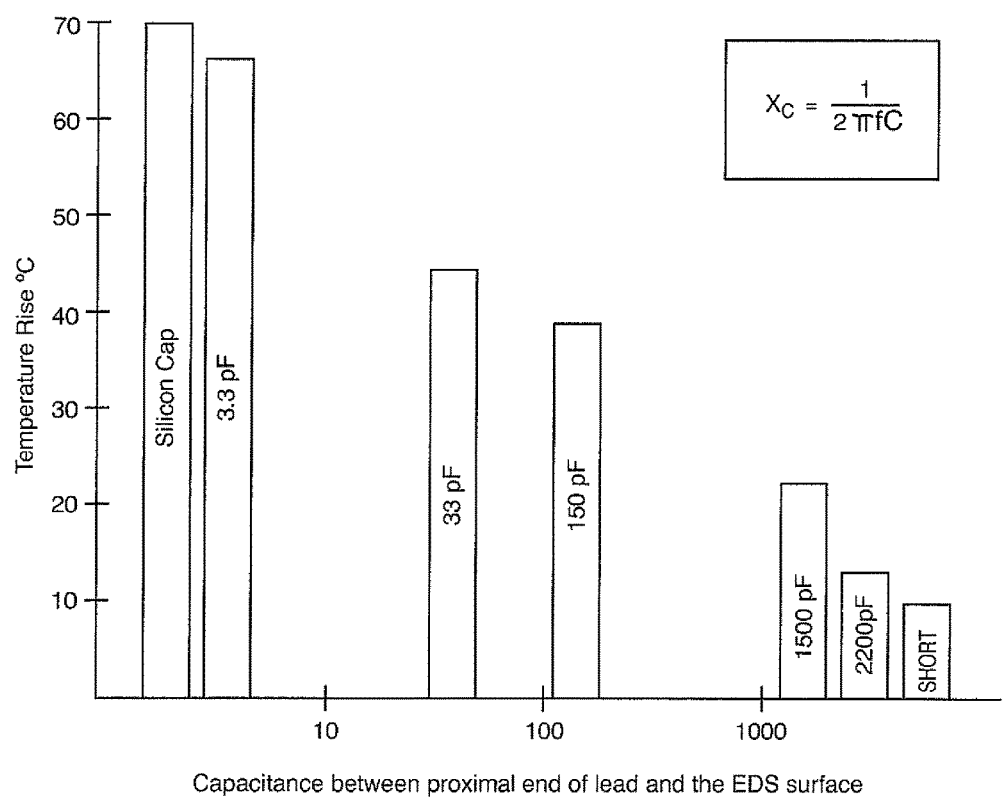
FIG. 44 illustrates a bar graph showing experimental data taken by the inventors with various types of abandoned leads.

FIG. 44 is a bar graph showing experimental data taken by the inventors with various types of abandoned leads. This data was taken in a human body phantom filled with an ASTM gel. Luxtron fiber optic probes were used to make precise temperature measurements of the distal electrodes. The temperature rise in degrees centigrade is shown on the Y axis. The X axis shows different types of proximal abandoned lead end terminations. On the far left, there is a silicone cap abandoned lead as shown which has a 70 degree temperature rise. When added to 37 degrees body temperature, one can see that this is a 107 degrees absolute temperature at the distal electrode, which is above the boiling point of water and is extraordinarily dangerous to human tissues. Looking at the far right hand side of the bar graph, one can see that frequency variable diverter capacitors of 1500 and 2200 picofarads are both very effective in reducing the amount of distal tip heating. The best case turned out to be a short to an AIMD housing. Accordingly, the short circuit is the preferred embodiment, in the present invention. The equation shown in FIG. 44 relates to capacitive reactance to the frequency and the capacitance value. Frequency appears as f in the dominator. The capacitance value is shown by C. The capacitive reactance $x_C$ is in ohms, the frequency is in hertz, and the capacitance is in farads. As one can see, with the capacitance appearing in the denominator, for higher capacitance values, capacitive reactance will be lower. This is why the highest capacitance values, 1500 picofarad and 2200 picofarad, act nearly as good as the short circuit.

Figure 45:
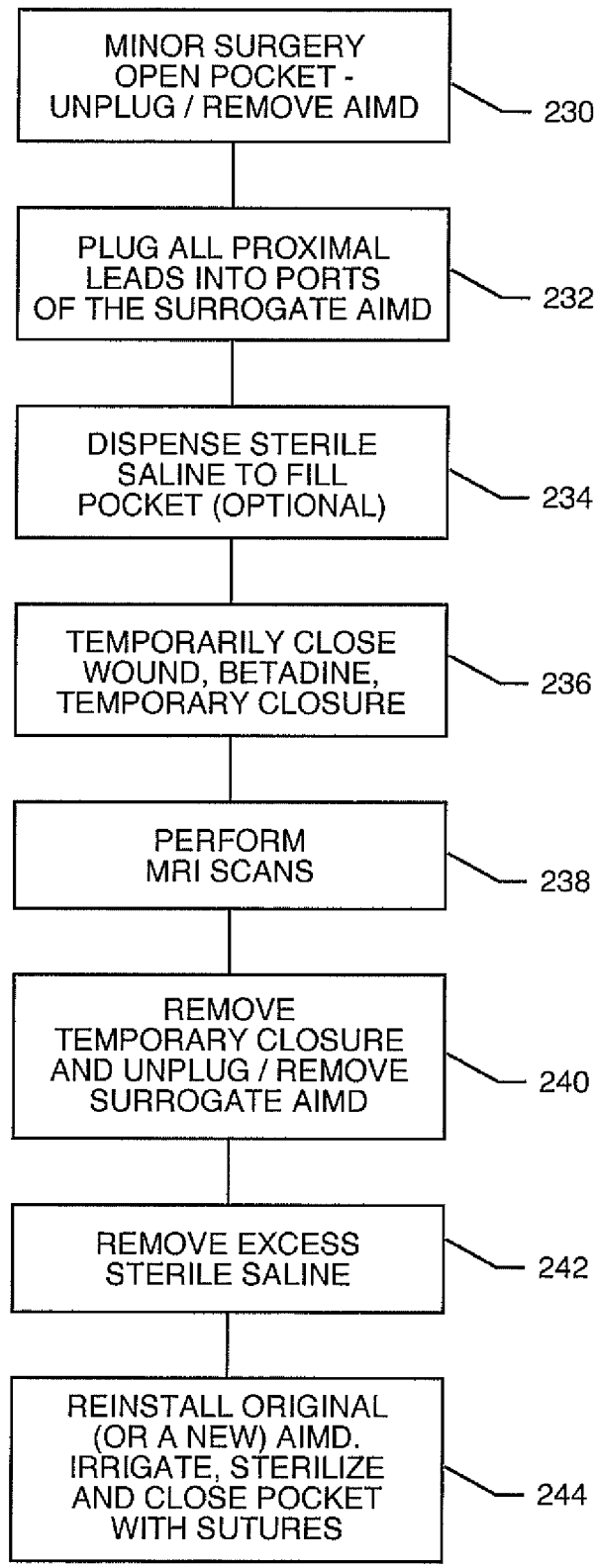
FIG. 45 is a flow chart illustrating a process of an embodiment of the present invention.

FIG. 45 is a flow chart illustrating the process of the present invention. In step 230, there is a minor surgery generally done as an outpatient under local anesthetic to open the pre-existing AIMD pocket. The AIMD is unplugged from its pre-existing leads. At this point, the AIMD is either discarded in the case that it has used up most of its battery life or, for a relatively new AIMD, it can be placed in a sterile container to be later reused. In step 232, the surrogate AIMD is installed and the proximal plugs of all the pre-existing leads are plugged into the ports of the surrogate AIMD. The surrogate AIMD can be any of the surrogate AIMDs are previously described in any of the previous drawings. This includes surrogate AIMDs wherein each of the connector leadwires are grounded to the AIMD housing or surrogate AIMDs where there is a frequency selective diverter. Step 234 is an optional step where the pocket is filled with sterile saline. The purpose of the sterile saline is to make sure that there is intimate thermal and electrical contact all around the surrogate AIMD EDS dissipation surface and that there are no voids. In step 236, the wound is temporarily sterilized and then closed with Steri-Strips™, Tegaderm™, various types of medical tapes, adhesives and the like. At this point, the patient is bandaged and is also ambulatory. The patient can then go to receive one or more MRI scans in step 238. After the MRI scans are completed, the patient again returns to the operating theater. As previously mentioned, the operating theater can be an outpatient surgical center, can be a cath lab, can be a hostile operating room or even a doctor's office. In step 240, the temporary closures are removed, at which time the surrogate AIMD is unplugged and taken out of the pocket. At this point in general, the surrogate AIMD will be disposed of. In some cases, the surrogate AIMD could be resterilized and reused. In step 242, any excess fluids, such as the sterile saline, are removed from the pocket, typically by using a vacuum procedure. In step 244, the original AIMD or new AIMD is installed using sterile procedures, at which time the pocket is permanently closed with stitches, sutures or the like. In some cases, it may not even be necessary to use stitches, for example, simple Steri-Strips may be used. Once the wound has healed and during a return visit of course, any stitches or Steri-Strips are removed and the patient is now released from care.

FIG. 46A illustrates a novel clip 246 (housing receiver) of the present invention. Attached and grounded to the clip 246 is a DF-1 (or equivalent) connector port 186. There is a set screw 190 which makes both electrical and mechanical contact to the male pin of the proximal connector (not shown). The clip 246 is designed to be tightly slipped over an AIMD housing 112.

FIG. 46B illustrates the novel clip 246 which has been clipped onto the AIMD housing 112. It is important that the clip be affixed very tightly and firmly such that there is both a strong mechanical attachment and a firm electrical attachment, such that high frequency RF energy will easily flow from the clip 246 into the overall energy dissipating housing 112. In a preferred embodiment, the clip 246 would be of titanium, stainless steel or similar strong and highly conductive biocompatible and non-toxic metal. There are a number of other metals that could be used. It is also a feature of the present invention that the clip could be plated with a suitable material such as gold or rhodium, which would facilitate a very low resistance electrical connection between the clip 246 and the EDS housing 112.

FIG. 46C is a top sectional view 46C-46C taken generally from FIG. 46B. FIG. 46C illustrates that there is an electrical connecting wire 248 that is routed from the set screw 190 and set screw housing 156 in the connector port 186. This connecting wire grounds the connector port contact 190 to the clip structure 246 at location 250. Once the clip is firmly attached to the AIMD housing 112, then another electrical connection is made 252 which completes the electrical circuit between the set screw 190 to the EDS housing and energy dissipating surface 112. Electrical contact 252 is understood to occur over the entirety of the contact between the clip and the housing 112. Referring once again to FIGS. 46A, 46B and 46C, it will be obvious that a single abandoned lead connector port 186 would not accommodate all possible pre-existing lead configurations. In other words, for the clip 246 approach to work, it must work in conjunction with a number of adapters.

Figure 47A:
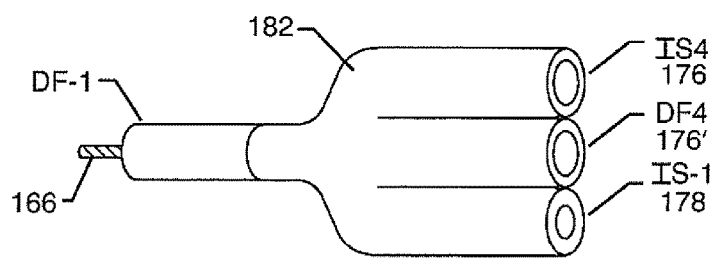
FIG. 47A illustrates an adapter of the present invention.

FIG. 47A illustrates such an adapter 182, which has a male DF-1 connector and mating electrical pin 166. When inserted, the electrical pin 166 will be mechanically and electrically fixed in place by the set screw 190 of FIG. 46C. In this particular case, the adapter 182 of FIG. 47A would allow for connection to a pre-existing IS4 lead 176, a pre-existing DF4 lead 176' and a pre-existing IS-1 lead 178.

Figure 47B:
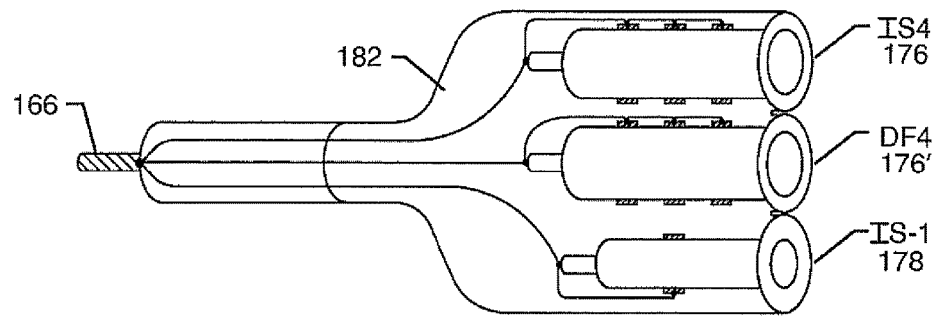
FIG. 47B is an internal electrical schematic view taken from FIG. 47A.

FIG. 47B is an internal electrical schematic view taken from FIG. 47A showing that all of the connector contacts of the three connector ports are all routed to the single contact pin 166 where they will be grounded after insertion into mating port 186.

Figure 48A:
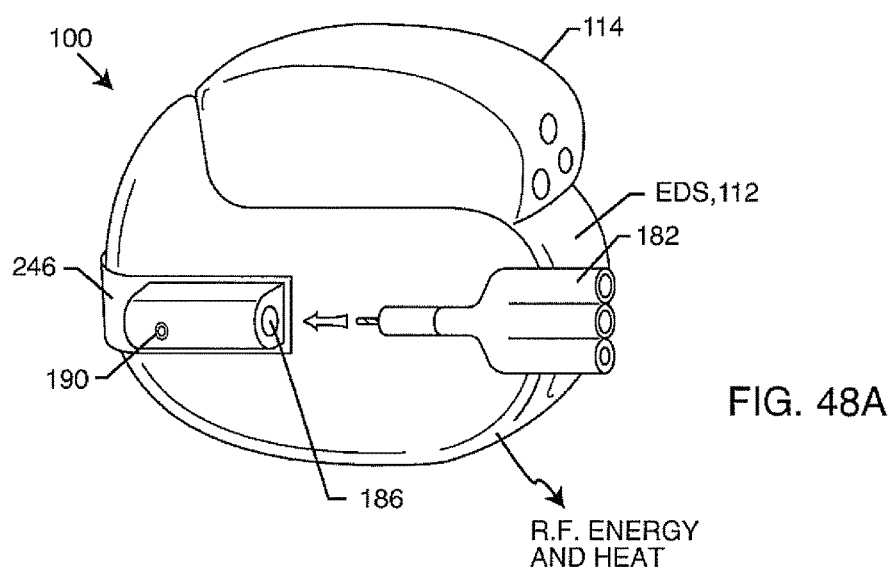
FIG. 48A illustrates the adapter previously described in FIG. 47A ready to be inserted into the novel clip assembly.

FIG. 48A illustrates the adapter 182 previously described in FIG. 47A ready to be inserted into the novel clip assembly 246.

Figure 48B:
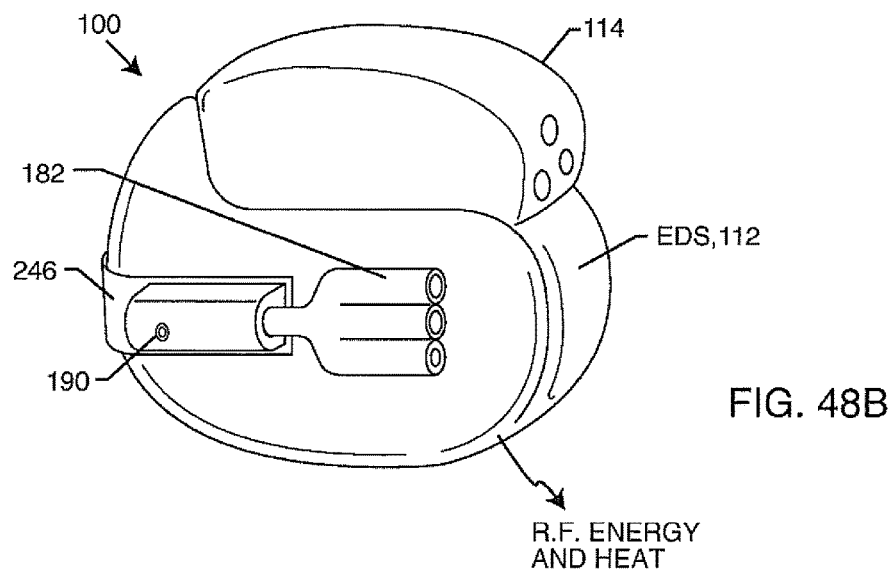
FIG. 48B is taken from FIG. 48A and shows the adapter fully inserted into the port.
Figure 49A:
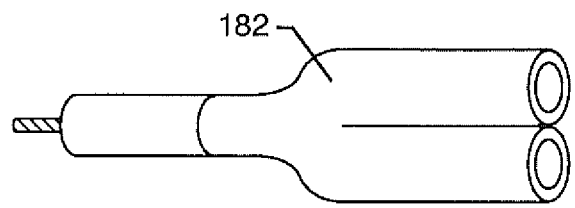
FIG. 49A is an embodiment of an adapter with two ports.
Figure 49B:
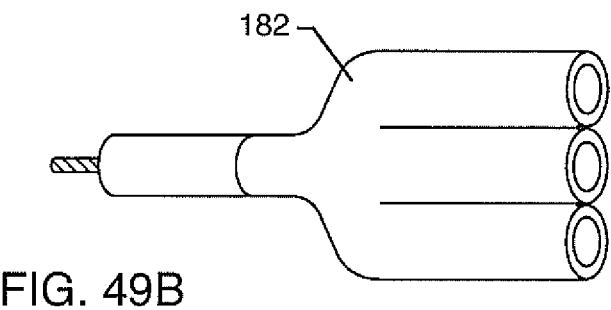
FIG. 49B is an embodiment of an adapter with three ports.
Figure 49C:
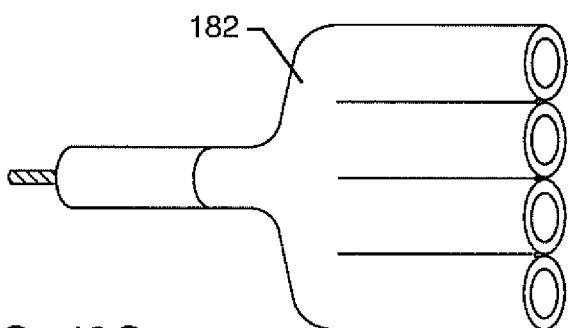
FIG. 49C is an embodiment of an adapter with four ports.
Figure 49D:
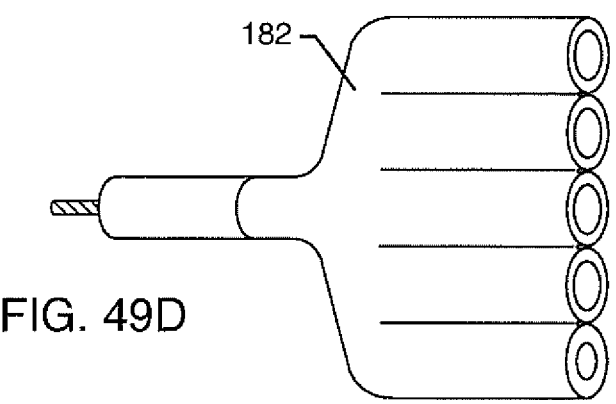
FIG. 49D is an embodiment of an adapter with five ports.

FIG. 48B is taken from FIG. 48A and shows the adapter 182 fully inserted into port 186. Set screw 190 is firmly torqued in place so that a sound electrical and mechanical connection is made to pin 166. One can see that the device is now ready for insertion back into the device pocket. In this case, a surrogate AIMD is not really needed. One can use the previously existing AIMD, which is generally non-MRI compliant. It becomes MRI compliant by turning it off and unplugging all of its leads. Since the MRI RF-pulsed energy is picked up on leads which act as antennas, there is little worry that the AIMD could be damaged or affected by being placed in the MRI field. As previously mentioned, the dangerous part of this are the pre-existing leads that could overheat during the MRI procedure. The novel clip 246 and adapter 182 allowed each of these pre-existing leads to be grounded to the AIMD housing 112, which acts as an energy dissipating surface which can prevent the pre-existing leads from overheating. After the MRI procedure is completed, it is a relatively simple matter to remove the adapter clip 246 and the adapter 182 and then once again plug the pre-existing leads back into the AIMD connector ports. At this point, the adapter clip 246 and the adapter 182 would either be discarded or resterilized and repackaged for future use.

FIGS. 49A through 49D illustrate various other types of adapters that may all be used in combination with a novel clip 246 previously described in FIGS. 46A, 46B and 46C. Referring once again to FIGS. 49A through 49D, one can see that there could be two, three, four, five or as many ports that are needed, which can be described as "n" ports. These ports may be any combination of DF-1, IS-1, DF4, IS4 or any other type neurostimulator lead that may be associated with any of the AIMDs which is being described in FIG. 1.

Figure 50A:
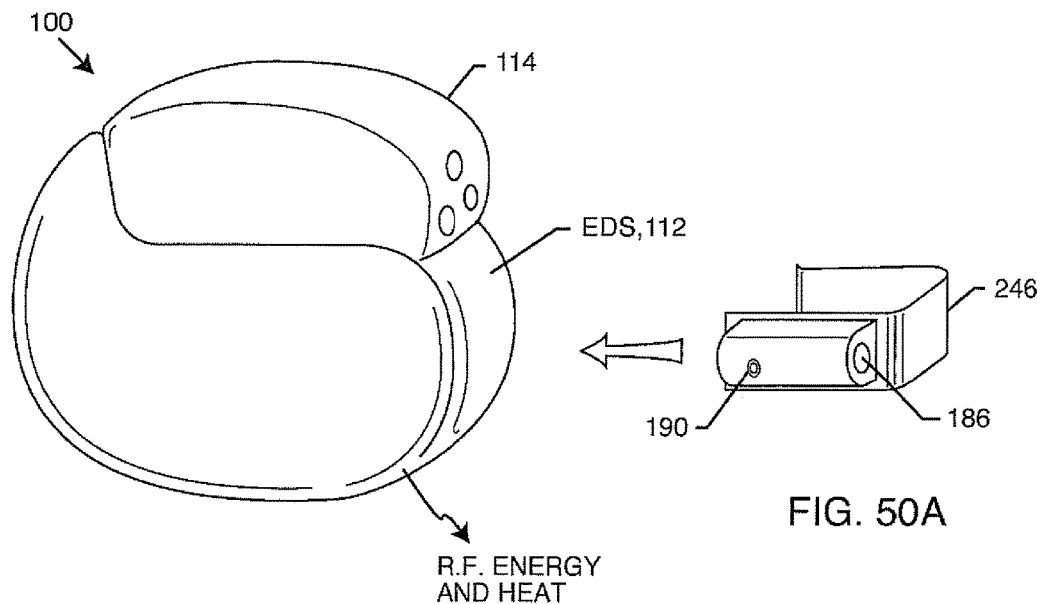
FIG. 50A illustrates the clip of FIG. 46A slipped on and attached to the AIMD housing 112 in the opposite direction.

FIG. 50A illustrates the clip of FIG. 46A slipped on and attached to the AIMD housing 112 in the opposite direction. The advantage of this arrangement is that the port 186 is aligned in the same direction as the pre-existing ports. This makes plugging in the pre-existing leadwires a little easier without the necessity for complex separation from surrounding tissues.

Figure 50B:
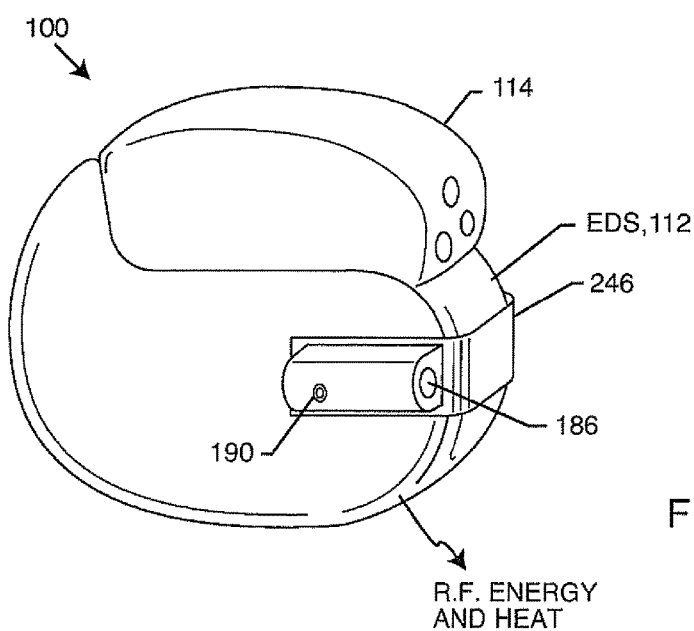
FIG. 50B illustrates the clip of FIG. 50A inserted firmly into place on the AIMD housing.

FIG. 50B shows the clip 246 of FIG. 50A inserted firmly into place on the AIMD housing 112.

Figure 51:
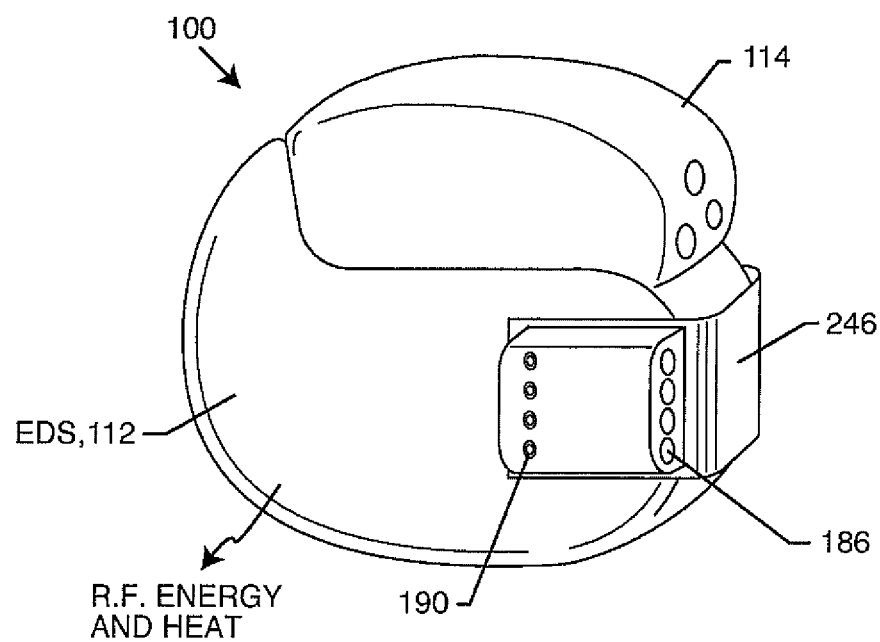
FIG. 51 illustrates the clip of FIG. 50 now with a multitude of ports.

FIG. 51 illustrates the clip 246 now with a multitude of ports 186. It will be understood by those skilled in the art that a novel clip 246 with a multitude of ports 186 eliminates the need for the adapters 182. The number of ports 186 can range from 1, 2, 3, 4, 5, 6, 7, 8 or any n number of ports in any orientation. Having one clip 246 with a multitude of ports 186 allows a single clip design to accommodate the varying needs shown and described herein and other needs not shown and described herein.

In review, an implantable medical device includes a housing and a header block body. A connector cavity is located within the header block and configured to attach to an implanted lead. A conductive leadwire is electrically connected to the connector cavity at one end and at its other end connected to or through a hermetic terminal of the implanted medical device housing. The conductive leadwire is grounded to the IMD housing. In a further embodiment, the connector cavity can include a plurality of connector cavities including IS-1, DF-1, IS4 or DF4 connector cavities. When a patient with a need for an MRI has a non-MRI approved AIMD it can be temporarily replaced with the present invention that can dissipate energy from the implanted leads during the MRI scan.

Although several embodiments have been described in detail for purposes of illustration, various modifications may be made to each without departing from the scope and spirit of the invention. Accordingly, the invention is not to be limited, except as by the appended claims.

What is claimed is:

1. A method for performing a Magnetic Resonance Imaging (MRI) scan when an active implantable medical device (an AIMD) is identified as possibly being scanned by an MRI device, the method comprising the steps of:
 a) identifying that an AIMD is positioned in a pre-existing AIMD pocket and that the AIMD is connected to at least one implanted lead;
 b) providing a surrogate implantable medical device (SIMD), the SIMD comprising:
  i) a thermally and electrically conductive housing;
  ii) at least one connector cavity configured to be attachable to an implantable lead; and
  iii) at least one conductive leadwire that is electrically connected to the at least one connector cavity and to the housing;
 c) surgically removing the AIMD from the pre-existing AIMD pocket;
 d) unplugging the at least one implanted lead from the AIMD;
 e) plugging the at least one implanted lead into the at least one connector cavity of the SIMD;
 f) implanting the SIMD into the pre-existing AIMD pocket;
 g) performing an MRI scan that scans the SIMD implanted in the pre-existing AIMD pocket;
 h) removing the SIMD from the pre-existing AIMD pocket;
 i) unplugging the at least one implanted lead from the SIMD;
 j) plugging the at least one implanted lead back into the AIMD or into a new AIMD; and
 k) implanting the AIMD or the new AIMD into the pre-existing AIMD pocket.

2. The method of claim 1, including providing the SIMD further comprising a header block body attached to the housing, wherein the at least one connector cavity is located in the header block body, and wherein the at least one conductive leadwire has a leadwire first end spaced from a leadwire second end, the leadwire first end being electrically connected to the at least one connector cavity in the header block body and the leadwire second end being electrically connected to the housing of the SIMD.

3. The method of claim 2, wherein the leadwire second end is connected to an inner or an outer surface of the housing of the SIMD.

4. The method of claim 1, further including the step of filling the pre-existing AIMD pocket with sterile saline before the step of performing the MRI scan.

5. The method of claim 1, further including the step of surgically closing the pre-existing AIMD pocket with stitches or sutures after the step of implanting the SIMD in the pre-existing AIMD pocket.

6. The method of claim 1, further including the step of temporarily surgically closing the pre-existing AIMD pocket with tape or an adhesive after the step of implanting the SIMD in the pre-existing AIMD pocket.

7. The method of claim 1, wherein the housing of the SIMD does not contain electronics.

8. A method for performing a Magnetic Resonance Imaging (MRI) scan when an active implantable medical device (an AIMD) having a conductive housing is identified as possibly being scanned by an MRI device, the method comprising the steps of:
 a) identifying that an AIMD is positioned in a pre-existing AIMD pocket and that the AIMD is connected to at least one implanted lead;
 b) providing an auxiliary implantable medical device (IMD), the auxiliary IMD comprising:
  i) a thermally and electrically conductive housing receiver that is configured to be electrically connected to a conductive housing of the AIMD;
  ii) a connector block body attached to the housing receiver;
  iii) at least one connector cavity located within the connector block body, wherein the at least one connector cavity is configured to be attachable to the at least one implanted lead; and
  iv) a conductive leadwire that is electrically connected to the at least one connector cavity located in the connector block body and to the housing receiver of the auxiliary IMD;
 c) attaching the auxiliary IMD to the conductive housing of the AIMD;
 d) unplugging the at least one implanted lead from the AIMD;
 e) plugging the at least one implanted lead into the at least one connector cavity located in the connector block body of the auxiliary IMD;
 f) performing an MRI scan that scans the auxiliary IMD attached to the AIMD implanted in the pre-existing AIMD pocket;
 g) unplugging the at least one implanted lead from the at least one connector cavity of the auxiliary IMD;
 h) detaching the auxiliary IMD from the AIMD and removing the auxiliary IMD from the pre-existing AIMD pocket; and
 i) plugging the at least one implanted lead back into the AIMD.

9. The method of claim 8, wherein the conductive leadwire is connected to an outer surface of the housing receiver of the auxiliary IMD.

10. The method of claim 8, wherein the conductive leadwire is connected to an inner surface of the housing receiver of the auxiliary IMD.

11. The method of claim 8, further including the step of filling the pre-existing AIMD pocket with sterile saline before the step of performing the MRI scan.

12. The method of claim 8, further including the step of surgically closing the pre-existing AIMD pocket with stitches or sutures after the step of attaching the auxiliary IMD to the AIMD implanted in the pre-existing AIMD pocket.

13. The method of claim 8, further including the step of surgically closing the pre-existing AIMD pocket with tape or an adhesive after the step of attaching the auxiliary IMD to the AIMD implanted in the pre-existing AIMD pocket.

14. The method of claim 8, wherein providing the auxiliary IMD further comprises providing an energy diverter element located in the connector block body, wherein the energy diverter element is conductively connected to the conductive leadwire between the at least one connector cavity and the housing receiver.

15. The method of claim 14, including selecting the energy diverter element from the group consisting of a short circuit, a resistor, a capacitor, and an L-C trap.

16. A method for performing a Magnetic Resonance Imaging (MRI) scan when an active implantable medical device (an AIMD) is identified as possibly being scanned by an MRI device, the method comprising the steps of:
 a) identifying that an AIMD is positioned in a pre-existing AIMD pocket and that the AIMD is connected to at least one implanted lead;
 b) providing a surrogate implantable medical device (SIMD), the SIMD comprising:
  i) a thermally and electrically conductive housing;

ii) a header block body attached to the housing;
iii) at least one connector cavity located within the header block body, wherein the at least one connector cavity is configured to be attachable to the at least one implanted lead;
iv) an energy diverter located inside the housing;
v) a hermetic terminal comprising a first conductive leadwire that is in non-conductive relation with the housing, wherein the first conductive leadwire comprises a first leadwire proximal end that is electrically connected to the energy diverter located inside the housing and a first leadwire distal end that is electrically connected to the at least one connector cavity in the header block body; and
vi) a second conductive leadwire comprising a second leadwire proximal end that is electrically connected to the energy diverter located inside the housing and a second leadwire distal end that is electrically connected to the housing of the SIMD;
c) surgically removing the AIMD from the pre-existing AIMD pocket;
d) unplugging the at least one implanted lead from the AIMD;
e) plugging the at least one implanted lead into the at least one connector cavity of the SIMD;
f) implanting the SIMD into the pre-existing AIMD pocket;
g) performing an MRI scan that scans the SIMD implanted in the pre-existing AIMD pocket;
h) removing the SIMD from the pre-existing AIMD pocket;
i) unplugging the at least one implanted lead from the at least one connector cavity of the SIMD;
j) plugging the at least one implanted lead back into the AIMD or into a new AIMD; and
k) implanting the AIMD or the new AIMD into the pre-existing AIMD pocket.

17. The method of claim 16, wherein other than the energy diverter, the housing of the SIMD does not contain electronics.

18. The method of claim 16, further including the step of filling the pre-existing AIMD pocket with sterile saline before the step of performing the MRI scan.

19. The method of claim 16, further including the step of surgically closing the pre-existing AIMD pocket with stitches or sutures after the step of implanting the SIMD in the pre-existing AIMD pocket.

20. The method of claim 16, further including the step of temporarily surgically closing the pre-existing AIMD pocket with tape or an adhesive after the step of implanting the SIMD in the pre-existing AIMD pocket.

21. The method of claim 1, further comprising the steps of:
a) identifying that the AIMD positioned in the pre-existing AIMD pocket is connected to at least two implanted leads, wherein a first one of the implanted leads is an active lead and a second one of the implanted leads is an abandoned lead;
providing a housing receiver that is configured for detachable mechanical and electrical attachment to the SIMD, wherein the housing receiver comprises at least one housing receiver connector cavity;
c) unplugging the active lead and the abandoned lead from the AIMD;
d) plugging the active lead into the at least one connector cavity of the SIMD and plugging the abandoned lead into the at least one housing receiver connector cavity,
e) wherein the step of implanting the SIMD into the pre-existing AIMD pocket further includes implanting the housing receiver which is mechanically and electrically attached to the SIMD into the pre-existing AIMD pocket,
f) wherein the step of performing an MRI scan that scans the SIMD further includes scanning the housing receiver mechanically and electrically attached to the SIMD, and
g) wherein the step of removing the SIMD from the pre-existing AIMD pocket further includes removing the housing receiver mechanically and electrically attached to the SIMD from the pre-existing AIMD pocket;
h) unplugging the active lead from the at least one connector cavity of the SIMD and unplugging the abandoned lead from the at least one housing receiver connector cavity; and
i) plugging the active lead back into the AIMD or into a new AIMD and plugging the abandoned lead back into the AIMD or into the new AIMD
prior to the step of implanting the AIMD or the new AIMD into the pre-existing AIMD pocket.

* * * * *